(12) United States Patent
Pageat

(10) Patent No.: US 6,169,113 B1
(45) Date of Patent: Jan. 2, 2001

(54) PIG APPEASING PHEROMONES TO DECREASE STRESS, ANXIETY AND AGGRESSIVENESS

(76) Inventor: Patrick Pageat, La Feniere, Route de Saint Saturnin, 84400 Apt (FR)

(*) Notice: Under 35 U.S.C. 154(b), the term of this patent shall be extended for 0 days.

(21) Appl. No.: 09/525,763

(22) Filed: Mar. 14, 2000

Related U.S. Application Data

(62) Division of application No. 09/010,515, filed on Jan. 21, 1998, now Pat. No. 6,077,867.

(51) Int. Cl.$^7$ ..................................................... B61A 31/20
(52) U.S. Cl. ............................................................. 514/558
(58) Field of Search ..................................... 514/558, 560

(56) References Cited

U.S. PATENT DOCUMENTS

| | | | |
|---|---|---|---|
| 6,015,712 | * 1/2000 | Monia et al. | 435/375 |
| 6,039,950 | * 3/2000 | Khwaja et al. | 424/195.1 |
| 6,054,481 | * 4/2000 | Pageat | 514/560 |
| 6,077,867 | * 6/2000 | Pageat | 514/558 |

FOREIGN PATENT DOCUMENTS

| | | |
|---|---|---|
| 0724832 | 8/1996 | (EP). |
| WO 93/16691 | 9/1993 | (WO). |
| WO 93/11987 | 12/1993 | (WO). |
| WO 94/15464 | 7/1994 | (WO). |

OTHER PUBLICATIONS

F.X. Roth et al., "On the Nutritive Value of Dried Potato and Maize Pulps for Pigs", Wirtschaftseigene Futter, 1975, vol. 21, No. 3, pp. 225–232.

E.S. Mosolova et al., "Fatty Acid Composition of Lipids in Colostrum, Milk and Whole Milk Susbstitutes (WMS) and Its Effect on the Quality of Production During the Feeding and Raising of Calves", S–kh. Biol., 1980, vol. 15, No. 4, pp. 589–591.

\* cited by examiner

*Primary Examiner*—William R. A. Jarvis
*Assistant Examiner*—Vickie Kim
(74) *Attorney, Agent, or Firm*—Young & Thompson

(57) ABSTRACT

A composition comprising a mixture of fatty acids such as linoleic, oleic and palmitic acids or derivatives thereof derived from secretions of mammalian mammary glands. This composition can be utilized to decrease stress, anxiety and aggressiveness in mammals.

5 Claims, 8 Drawing Sheets

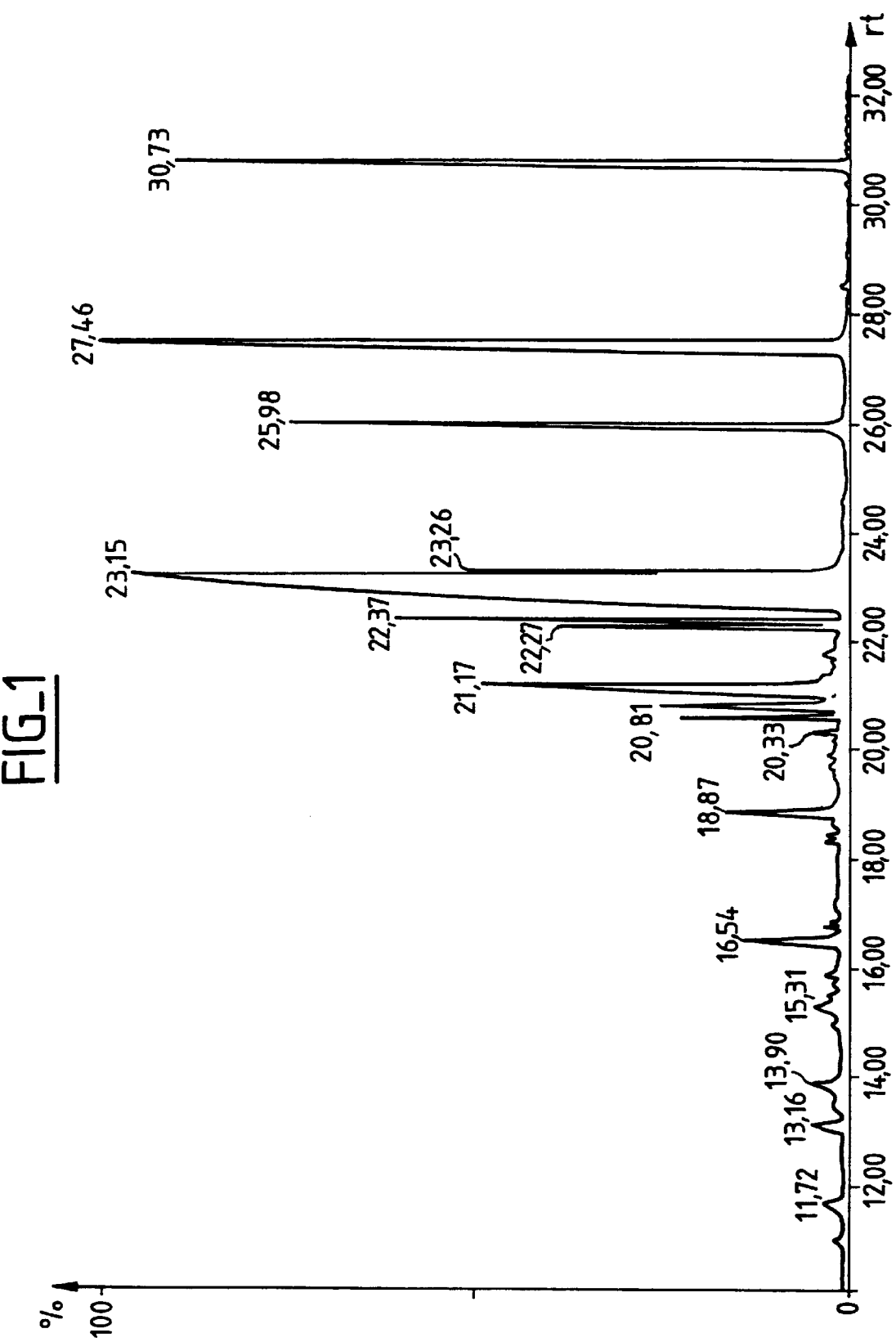

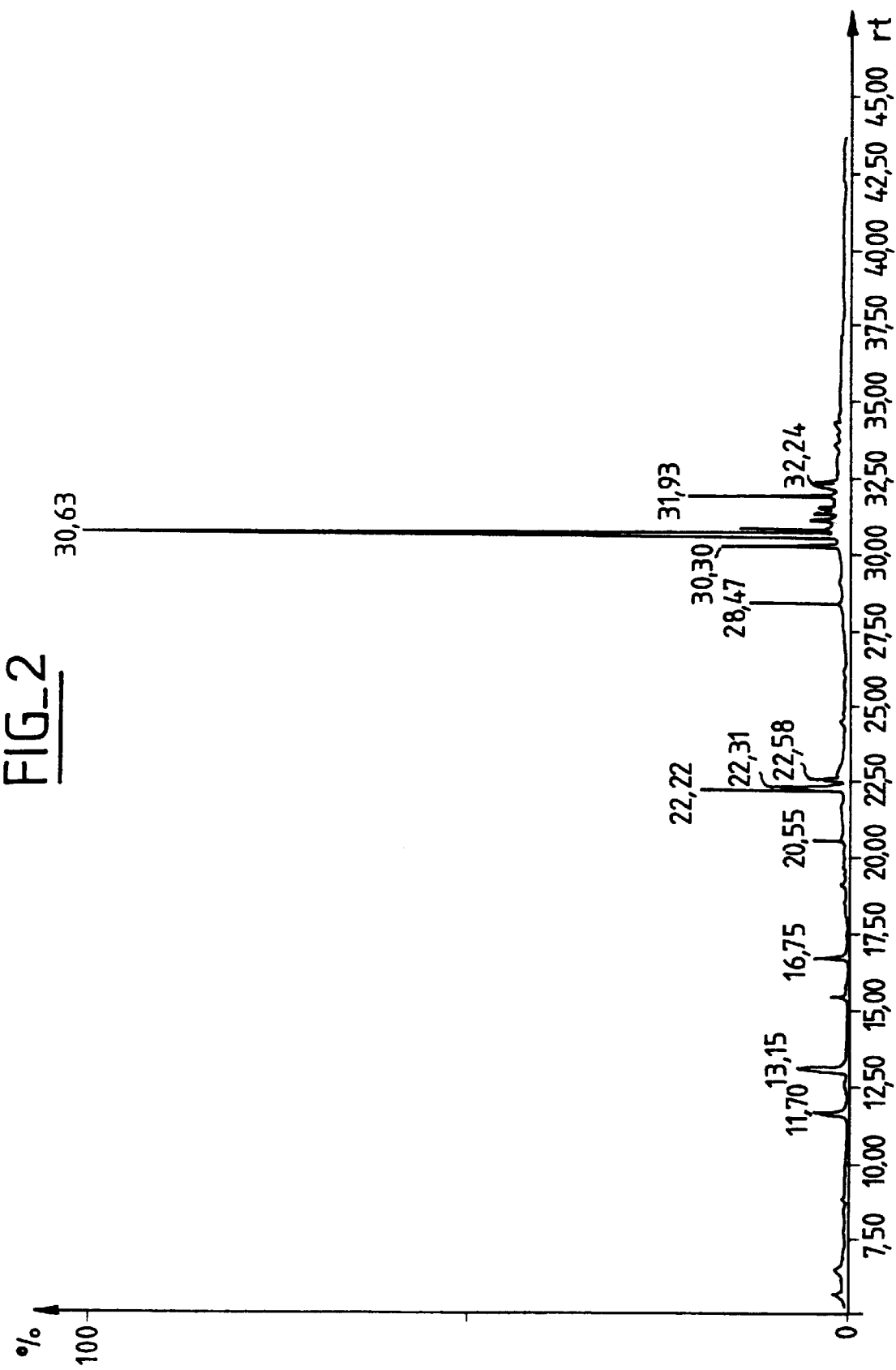
FIG_2

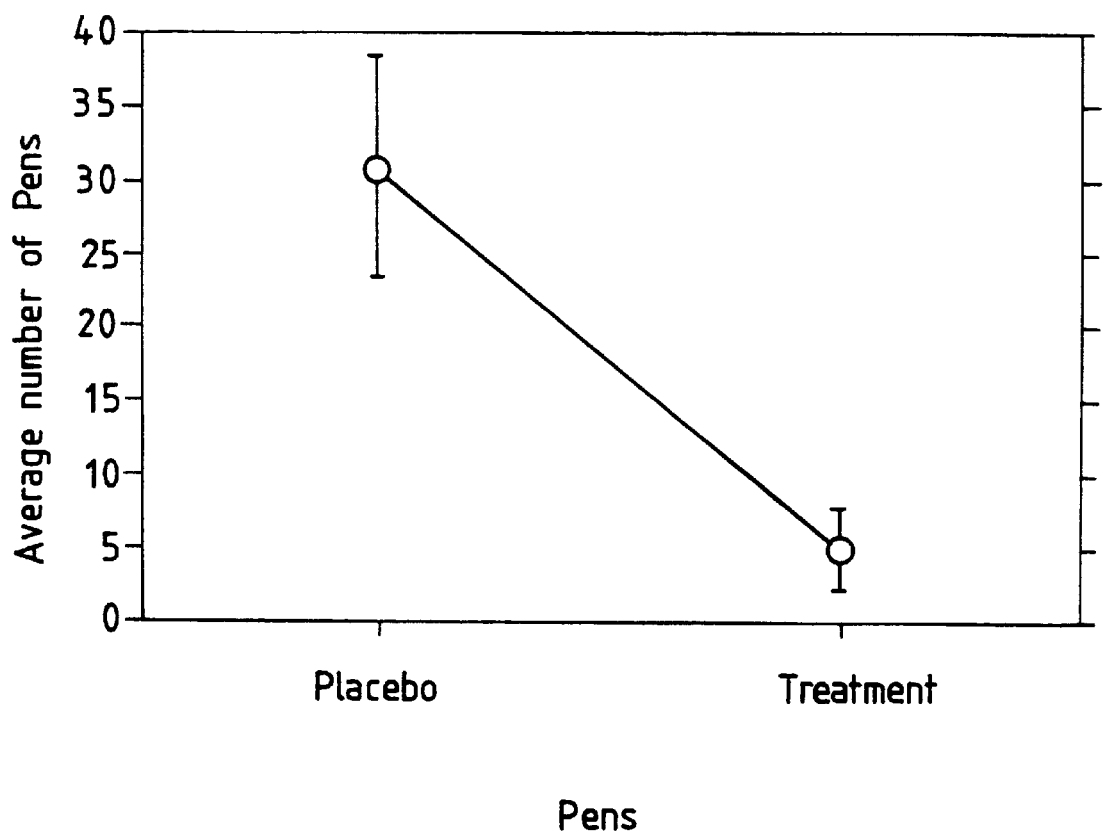

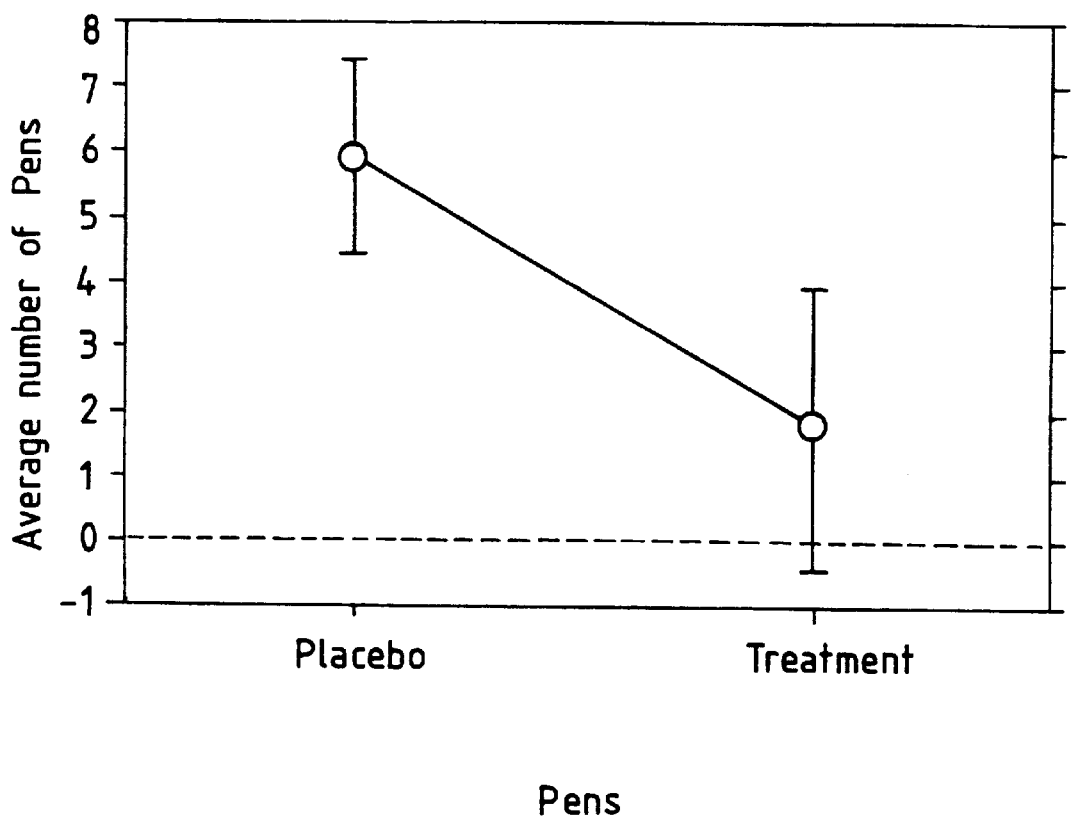

FIG_5
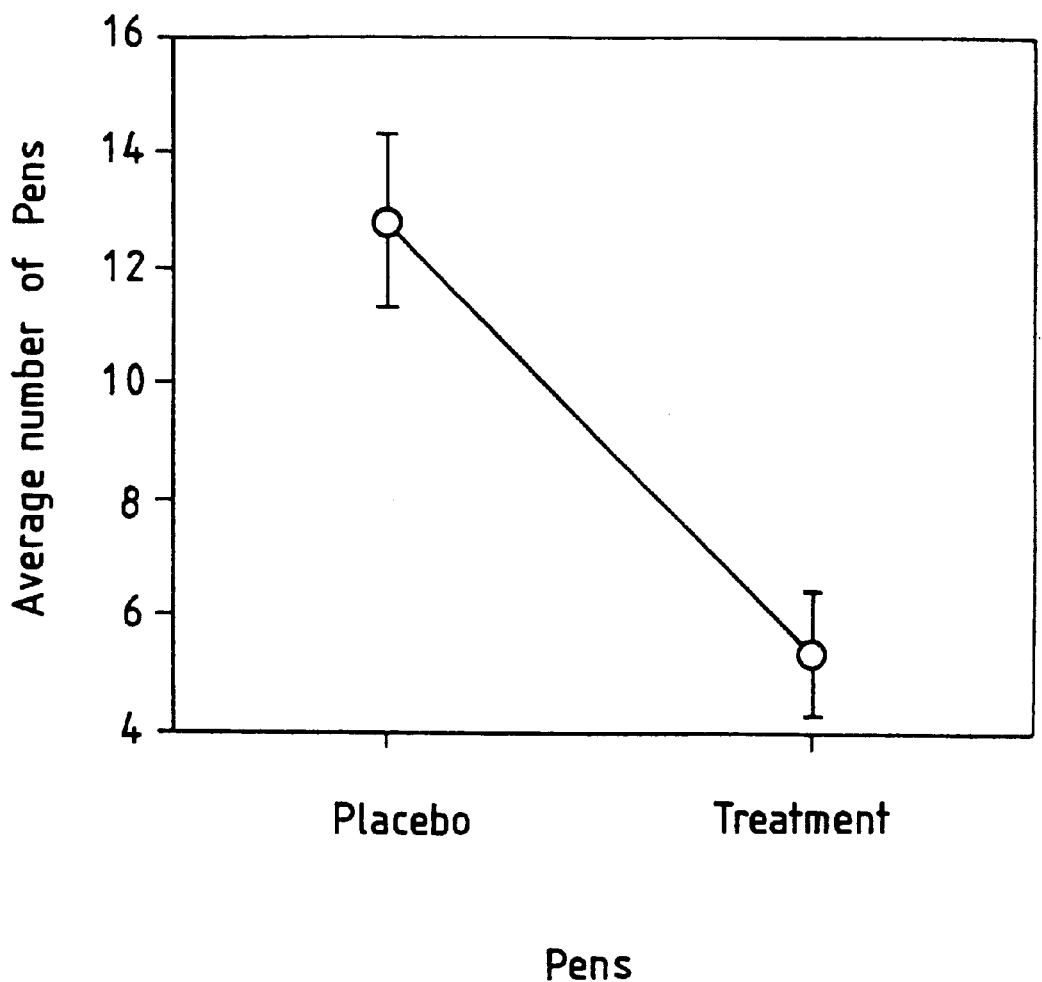

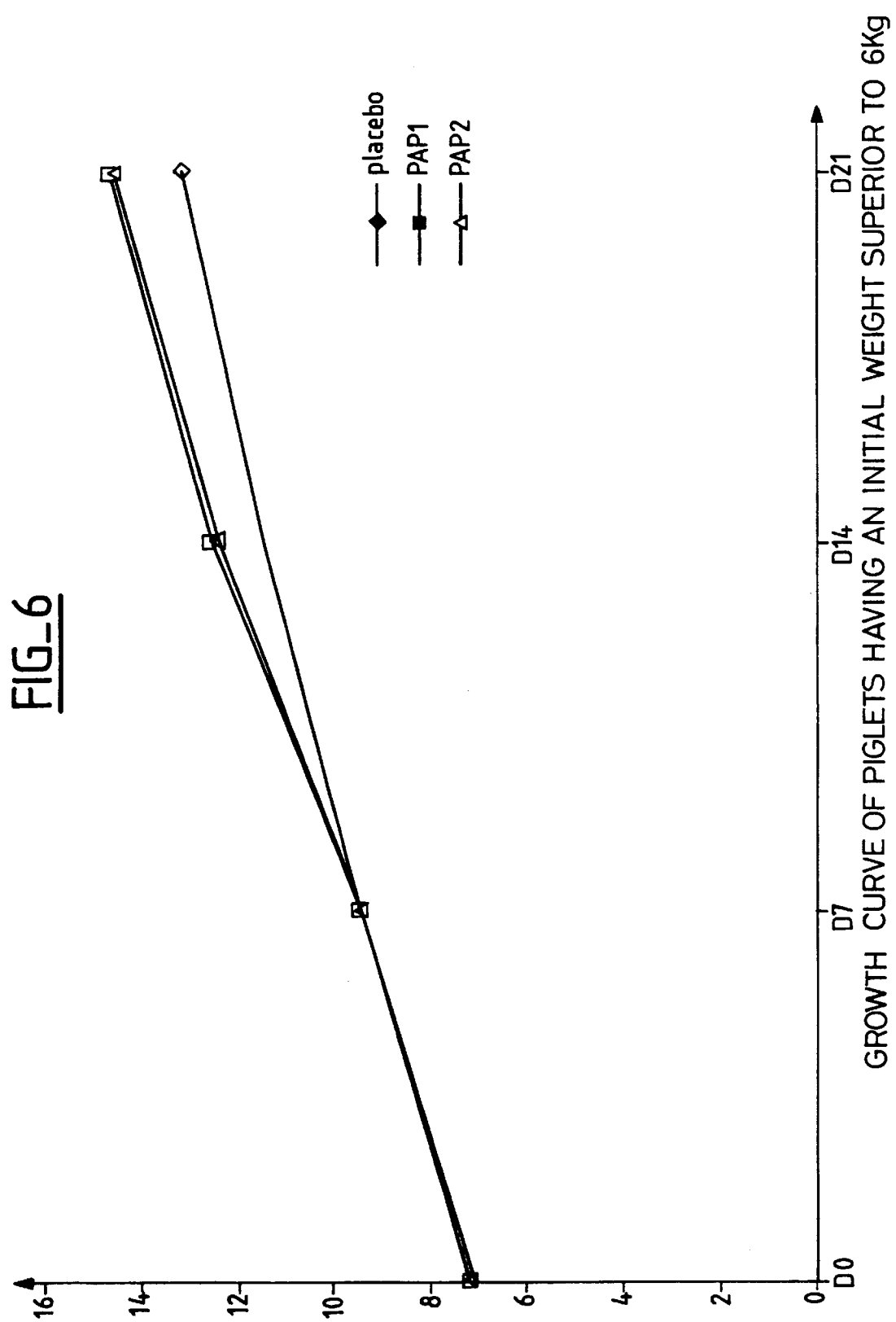

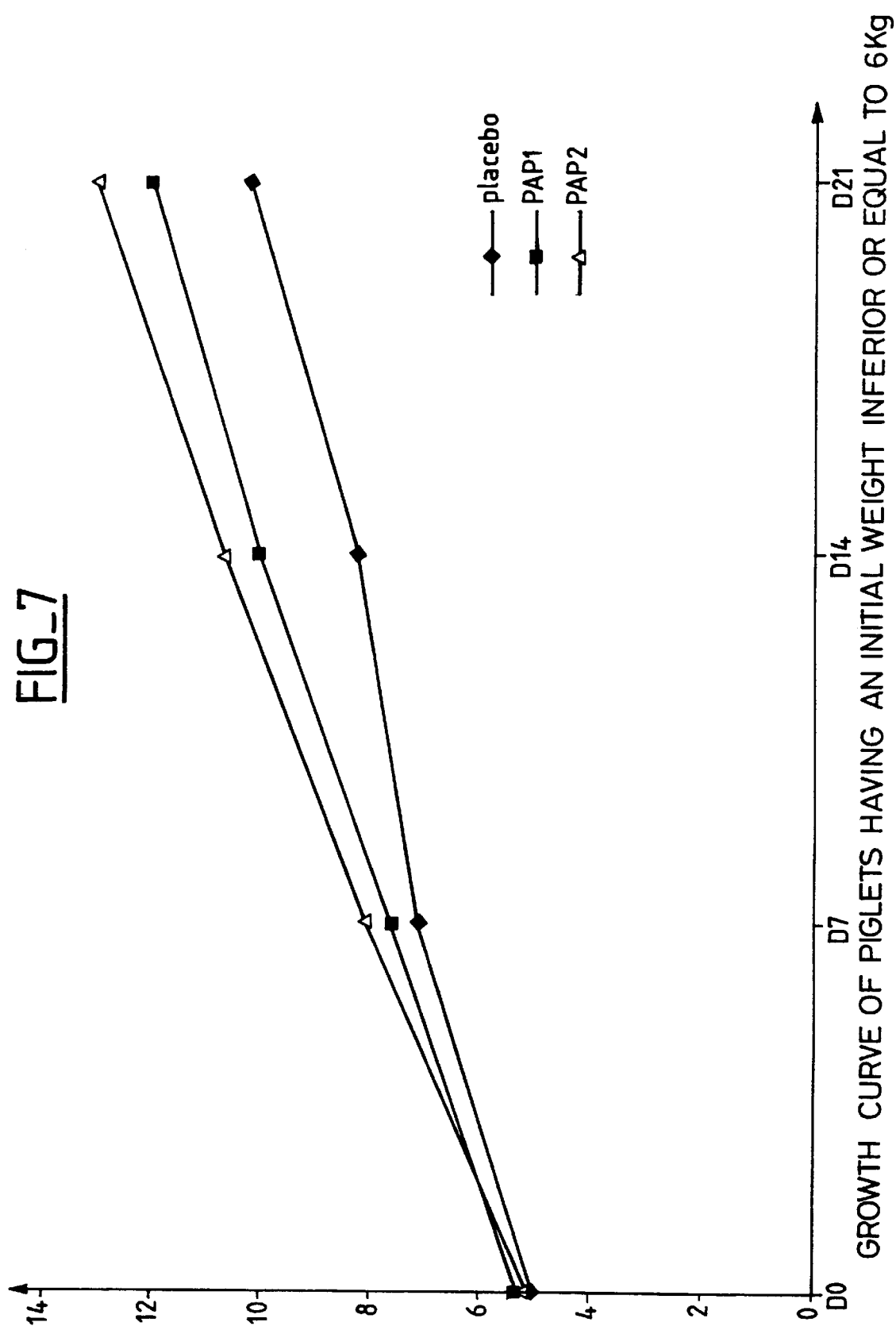
FIG_7
GROWTH CURVE OF PIGLETS HAVING AN INITIAL WEIGHT INFERIOR OR EQUAL TO 6Kg

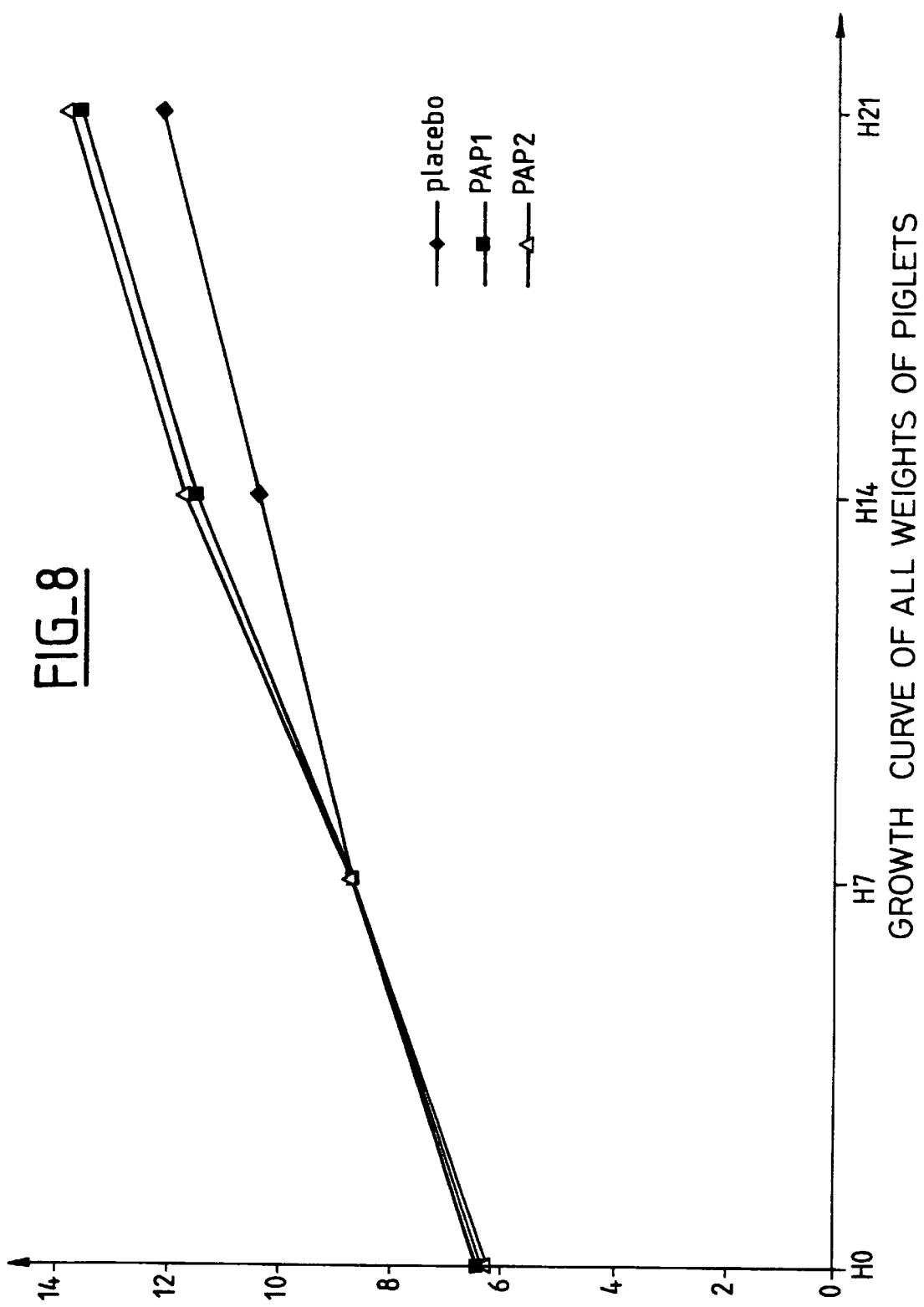

PIG APPEASING PHEROMONES TO DECREASE STRESS, ANXIETY AND AGGRESSIVENESS

CROSS-REFERENCE TO RELATED APPLICATIONS

This application is a division of application Ser. No. 09/010,515, filed Jan. 21, 1998 now patented, U.S. Pat. No. 6,077,867.

FIELD OF THE INVENTION

The present invention relates to a composition comprising a mixture of fatty acids or derivatives thereof derived from secretions of mammalian mammary glands. This composition can be utilized to decrease stress, anxiety and aggressiveness in mammals.

BACKGROUND AND PRIOR ART

Stress, by definition, is the reaction of an animal body to forces of deleterious nature, infections and various abnormal states that tend to disturb homeostasis.

Animals exposed to stress respond with changes in the activity of the autonomic and neuroendocrine systems and in behavior. The activation of these biological systems is a prerequisite for the animal to cope with stress and thus is the principal resource that will provide the adequate biological defense against a threat that challenges the homeostasis of the animal. Moberg, G. P. *Animal Stress*, pp. 27–49 (1985); Vogel, W. H. *Neuropsychobiology*, 13 pp. 1290135 (1985).

In animals, including humans, stress stimulates the release of Adenocorticotropic hormone (ACTH) which controls the release of cortisol from the adrenal cortex.

In humans, stress can lead to medical problems such as ulcers and erosions, acute gastritis and diarrhea. Onsets of erythrocytosis, inflammatory bowel disease, heart attacks and ischemia are influenced by stress. In fact, there is a valid clinical impression that psychic or emotional stress and anxiety are associated with precipitation of overt ischemic heart diseases and sudden death. See, Harrison's Principles of Internal Medicine,, McGraw-Hill Inc., 12th Edition (1991).

Animals, such as pigs, dogs, cattle and the like are also influenced by changes in their environment. The result of animals being taken out of their environment, being herded together and transported often results in the animals being stressed. As a consequence, pathological disorders, mortality, delays in growth and disorders in behavior often occur in stress-related conditions. Disorders in behavior often lead to aggressive fighting when animals are mixed.

It is well known, for instance, that social stress is common during the growing period. This social stress often occurs as a consequence of separation from the dam, moving to a new environment and mixing with unacquainted younglings. In the field of animal husbandry, social stress occurs often in piglets.

This social stress often leads to agonistic behavior among animals, which consists of fighting or trying to escape. For example, piglets begin fighting within hours of birth and when pigs of any age meet, a fight is likely to occur. See, McGlone, JJ, *Journal of Animal Science*, 68:11 pgs. 86–97 (1990)

In fact, it has been observed that when pigs fight, they assume a particular posture wherein the pigs face one another with their shoulders pressed together. The objective of this position is to place bites on the ears of their opponents. The winner places about three times as many bites on the ear than the loser. While pigs rarely kill one another, the fighting often inflicts large wounds during the course of the battle, especially on the head, ears, neck and shoulders. McGlone, supra suggest that a pheromone is released during the end of a fight that signals submission.

Because of the varied forms and effects of aggression associated with stress and especially anxiety related problems, clinical experts have sought to cure or prevent these problems by treatment with psychotropic or neuroleptic drugs. Among the categories of drugs that were used to stress-related problems should be mentioned amperazide, chlorpromazine, azaperone, haloperidol, properciazine, prochlorperazine, diazepam, meprobamate, phenobarbital, phenothiazines and butyrophenones.

For example, Dantzer, R. in *Veterinary Science Communications*, 1 pgs. 161–169 (1977) reviews the use of neuroleptic drugs for fattening animals to improve production, as well as the use of tranquilizers to reduce the problems of stress.

Kyriakis & Anderson in *J. Vet. Pharmacol. Therap.*, 12, pgs 232–236 (1989) disclose the use of amperozide to modify social behavior and treat wasting pig syndrome. Wasting pig syndrome is a phenomenon whereby stressed piglets degenerate to death.

However, no one knows the long-term effects of these drugs when humans consume meat taken from animals that have been given the various drugs. In fact, in many cases, the administration of neuroleptic drugs in the feeds to fatten animals does not directly improve production and have adverse effects such as slower weight increase, a decline in milk production in dairy cows and a decline in laying eggs in the case of poultry. In some cases delayed sexual maturity has also been observed. Dantzer, supra.

By definition, pheromones are substances released by the body that cause a predictable reaction by another individual of the same species.

A number of different glands are known to produce pheromones in male mammals such as the submaxillary salivary glands, the parathyroid glands and the sebaceous glands.

Pheromones that are secreted in the submaxillary salivary and parathyroid glands in males, are used to mark females during courtship. In boars, the secretion of these glands results in agonistic behavior. These secretions are known to contain a mixture of androstenol and androsterone.

The use of genital pheromones to augment artificial insemination in pigs has been described, in example by Komonov et al., Russia application No. 1720640 A1, wherein said genital pig pheromone comprises butyric acid, acetic acid, and capric acid. This reference fails to describe the use of a genital pheromone to reduce stress and anxiety.

Maternal odors are known to have an attractive effect on piglets and play an important role in maternal-neonatal behavior in pigs. Piglets are known to ingest maternal feces and are attracted to this substance. Tesch and McGlone (*J. Anim. Sci.* 68, pgs 3563–357 (1990). Thus olfactory communication between the sow and her litter occurs through the production of attractive substances.

Due to this maternal attraction, when piglets are separated from their mothers, stress-related behavior often results which leads to increase in fighting, and stress-related weight loss.

This phenomenon is also observed in other mammals such as humans, when an infant is separated from its mother leading to anxiety in the child.

Thus, to treat stress and stress-related symptoms without using the various tranquilizing drugs in mammals has not yet been achieved.

Thus, it is an object of the present invention to provide an alternative treatment for stress and anxiety in mammals.

Another object of the present invention is to provide a novel composition which treats stress without having the side effects of tranquilizing drugs.

Yet another object of the present invention is to provide a treatment to reduce aggressive behavior in mammals.

Yet another object of the present invention is to provide a composition that enhances weight gain in mammals.

Yet another object of the present invention is to reduce mortality and morbidity during infectious events in mammals.

Still another object of the present invention is to reduce feed conversion efficiency; i.e., the ratio of food consumed/weight gained.

These and other objects are achieved by the present invention as evidenced by the summary of the invention, description of the preferred embodiments and the claims.

SUMMARY OF THE PRESENT INVENTION

In one of the composition aspects, the present invention provides a composition comprising pheromonal secretions obtained from the skin around mammalian mammary glands.

In another composition aspect the present invention provides a basic pheromonal composition comprising palmitic acid, oleic acid, linoleic acid and derivatives thereof which composition has an appeasing effect in all mammals.

In yet another composition aspect the present invention provides a basic pheromonal composition comprising palmitic acid, oleic acid, palmitoleic acid, linoleic acid and derivatives thereof which composition also has an appeasing effect in all mammals.

In another composition aspect, the present invention provides a composition comprising capric acid, lauric acid, myristic acid, palmitic acid, palmitoleic acid, oleic acid, linoleic acid and derivatives thereof in a solution.

In a preferred embodiment, the present invention provides a composition comprising between about 18% to 31.2% (w %/w %) palmitic acid, about 34.3% to 47.2% (w %/w %) linoleic acid, about 28.7% to 42.8% (w %/w %) oleic acid and derivatives thereof.

In yet another preferred embodiment, the present invention provides a composition comprising between about 18% to 31.2% (w %/w %) palmitic acid, about 34.3% to 47.2% (w %/w %) linoleic acid, about 8.7% to 16% palmitoleic acid, about 15.7% to 30.7% (w %/w %) oleic acid and derivatives thereof.

In another preferred embodiment the present invention provides a solution comprising between 0.5% to 3.5% (w %/w %) capric acid, 2.8% to 8.7% (w %/w %) lauric acid, 3.9% to 9.6% (w %/w %) myristic acid, 7.5% to 13.8% (w %/w %) palmitoleic acid, 15.5% to 26.8% (w %/w %) palmitic acid, 29.5% to 40.6% (w %/w %) linoleic acid, 13.5% to 26.4% (w %/w %) oleic acid and derivatives thereof.

In another embodiment, the present invention relates to a process to treat stress in a mammal, said process comprising the step of: administering to a mammal in need of such treatment a pheromonal composition comprising secretions derived from the skin around mammalian mammary glands.

In another preferred embodiment, the present invention relates to a process of treating domestic mammals during transportation to eliminate their anxiety, said process comprising the steps of: administering to a mammal in need of such treatment a pheromonal composition comprising secretions derived from the skin around mammalian mammary glands.

In yet another preferred embodiment, the present invention relates to a process of treating weight loss in mammals, said process comprising administering to a mammal a need of such treatment a pheromonal composition comprising secretions derived from mammalian mammary glands.

In another embodiment, the present invention relates to a process to reduce mortality and morbidity during infection in a mammal, said process comprising the step of: administering to a mammal in need of such treatment a pheromonal composition comprising secretions derived from the skin around mammalian mammary glands.

In another embodiment, the present invention relates to a process to improve feed conversion in a mammal, said process comprising the step of: administering to a mammal in need of such treatment a pheromonal composition comprising secretions derived from the skin around mammalian mammary glands.

BRIEF DESCRIPTION OF THE DRAWINGS

FIG. 1 is a gas chromatography/mass spectroscopy spectrum profile of the components found in secretions from suckling sows.

FIG. 2 is a gas chromatography/mass spectroscopy spectrum profile of the components found in secretions from pregnant sows.

FIG. 3 is a graph illustrating the fresh wounds inflicted on piglet ears at 5 hours with pheromone treatment and placebo in piglets that were placed in a pen.

FIG. 4 is a graph illustrating the fresh wounds inflicted on piglet ears at 72 hours with pheromone treatment and placebo in piglets that were placed in a pen.

FIG. 5 is a graph illustrating the duration of fighting between piglets with pheromone treatment and placebo in piglets that were placed in a pen.

FIG. 6 is a growth curve of piglets having an initial weight superior to 6 kg with pheromone treatment and placebo.

FIG. 7 is a growth curve of piglets having an initial weight inferior or equal to 6 kg with pheromone treatment and placebo.

FIG. 8 is a growth curve of all weights of the piglets with pheromone treatment and placebo.

DETAILED DESCRIPTION OF THE PREFERRED EMBODIMENTS

As used herein, the word "mammal" encompasses any group of vertebrates the females of which have milk-secreting glands, including man. Examples of mammals include, but are not limited to, cats, humans, dogs, pigs, rats, cattle, horses, apes, chimpanzees and the like.

By "stress" is meant the reaction of an animal body to forces of deleterious nature, infections and various abnormal states that tent to disturb homeostasis. This reaction may be a physical reaction or an emotional reaction including anxiety.

By "anxiety" is meant an apprehension of anger and dread accompanied by restlessness, tension and the like, which is a reactional status characterized by a high probability to provide behavioral and emotional responses of fright. In neurophysical terms, this anxious state is accompanied by an hyperactivity of the noradrenergic and serotonin systems.

By "pheromone" is meant a substance released by the body of a particular species that causes a predictable reaction by another individual of the same species, which substance may serve, for example, as a specific attractant, social communicator, sexual stimulant and the like.

By "agonistic behavior" is meant of, relating to, or being aggressive or defensive social interaction between individuals of the same species such as fighting, fleeing or submitting.

By "stress-associated diseases" is meant any disease whose symptoms increase due to stress.

By "reducing morbidity and mortality during infection" is meant that death and diseased states are reduced such that the mammal has a better chance of survival.

By "improve feed conversion efficiency" means the reduction of the ratio in food consumption/weight gained.

By the term "solution" is meant a solid that is dispersed through a liquid either by being dissolved in it or being in suspension.

By "appeasing effect" is meant a reduction of fear, apprehension, anxiety, as well as the behavioral and physical consequences associated with stress. The behavioral consequences associated with stress include tremor, vocalization, flight, agression, displacement activities and the like. The physical consequences associated with stress include changes in heart rate, changes in levels of epinephrine, norepinephrine, ACTH, cortisol, glucose and the like. In animals used as a source of food, this definition includes husbandry parameters such as growth weight and food conversion efficiency.

By "basic pheromonal composition" is meant a pheromonal composition that can be used cross-species in all mammals and comprises as a main active ingredient at least three fatty acids.

By "enhancer composition" is meant an active pheromonal composition that is species-specific in mammals and which can be used to enhance or act synergistically with the basic pheromonal composition to increase the effectiveness in specific species of the "basic composition."

More specifically, the present invention relates to the identification of a basic pheromonal composition that is derived from secretions around the mammary glands of sows and more particularly the secretions of sows that are either pregnant or suckling.

The compositions of the present invention are pheromonal in origin and made up of volatile molecules, the essential components of these molecules being amines and fatty acids from indolic derivatives, as well as esters of these amines and fatty acids.

More specifically, the basic composition of the present invention comprises a mixture of at least three fatty acids; namely palmitic acid, linoleic acid and oleic acid, which represent between about 65% to 95% (w %/w %) of the total composition, the remaining ingredients being nontoxic filler compounds, such as fatty acids, alcohols, amines, squalene and glycerol. More particularly, caproic acid, azelaic acid, propionic acid, geraniol, octadecatrianol, hexacosanol, trimethylamine and methylamine.

The basic composition can also be attached to a chemical carrier provided that the bioactive structure of the fatty acids is preserved. Such carrier molecules include, but are not limited to resins, liposomes, crown compounds, carrier proteins and the like.

The fatty acids can be used in their pure form, i.e., as a free fatty acid, as well as their derivative form such as esters of fatty acids or salts of fatty acids.

This basic composition has been found to have an appeasing effect in all mammalian species and can be used to relieve stress, anxiety, reduce agressive behavior and the like, as set forth above.

For this basic pheromonal composition, it is preferable to use between about 18% to 31.2% (w %/w %) palmitic acid, about 34.3% to 47.2% (w %/w %) linoleic acid and about 28.7% to 42.8% (w %/w %) oleic acid; more preferably, between about 18% to 31.2% (w %/w %) palmitic acid, about 43.3% to 47.2% (w %/w %) linoleic acid, 8.7% to 16% palmitoleic acid and about 15.7% to 30.7% (w %/w %) oleic acid.

The basic pheromonal composition can be diluted in various solutions, as set forth below and can also be used in various forms.

An enhancer composition containing between 5% to 35% (w %/w %) can also be added to the basic pheromonal composition, if desired. This enhancer composition comprises volatile organic compounds and mixtures thereof. This enhancer composition may be species-specific in nature and may vary according to the mammalian species selected for use of the present invention.

The compounds that may be used in the enhancer composition, include, but are not limited to amines and fatty acids from indolic derivatives, esters of these amines and fatty acids, ketones such as acetone, alcohols, sterols and the like.

Besides the basic pheromonal composition and the enhancer composition a preferred embodiment of the present invention relates to a composition comprising free fatty acids, including decanoic acid, such as capric acid, dodecanoic acid, such as lauric acid, tetradecanoic acid, such as myristic acid, hexadecanoic acid, such as palmitic acid, cis-9-octadecanoic acid, such as oleic acid, linoleic acid and palmitoleic acid. Derivatives of these fatty acids can also be utilized in the present invention. More specifically these derivatives are esters of the fatty acids or salts of fatty acids.

This composition may be in the form of a solution, aerosol spray, gel, slow release matrix, shampoo, microencapsulation product and the like.

The concentration of the above-mentioned fatty acids may vary depending upon the final form of use. However, the concentrations of the specific fatty acids that may be utilized and their concentration may be ascertained and tested according to the methods set forth in the present invention.

In another preferred embodiment of the present invention, contains a solution comprising about 0.5% to 3.5% (w %/w %) of capric acid, 2.8% to 8.7% (w %/w %) of lauric acid, 3.9% to 9.6% (w %/w %) of myristic acid, 7.5% to 13.8% (w %/w %) of palmitoleic acid, 15.5% to 26.8% (w %/w %) of palmitic acid, 29.5% to 40.6% (w %/w %) of linoleic acid and 13.5% to 26.4% (w %/w %) of oleic acid.

In another preferred embodiment, the composition in solution of the present invention comprises 0.5% to 3.5% (w %/w %) of capric acid, 2.8% to 8.7% (w %/w %) of lauric acid, 3.9% to 9.6% (w %/w %) of myristic acid, 15.5% to 26.8% (w %/w %) of palmitic acid, 29.5% to 40.6% (w %/w %) of linoleic acid and 24.7% to 36.8% (w %/w %) of oleic acid.

In a most preferred embodiment of the composition in solution of the present invention contains 2% (w %/w %) capric acid, 5.3% (w %/w %) lauric acid, 6.2% (w %/w %)

myristic acid, 11.2% (w %/w %) palmitoleic acid, 20.5% (w %/w %) palmitic acid, 35.2% (w %/w %) linoleic acid and 19.6% (w %/w %) oleic acid.

Yet another most preferred embodiment of the invention the composition in solution contains 2% (w %/w %) capric acid, 5.3% (w %/w %) lauric acid, 6.2% (w %/w %) myristic acid, 20.5% (w %/w %) palmitic acid, 35.2% (w %/w %) linoleic acid and 19.6% (w %/w %) oleic acid.

The fatty acids, which are generally solid in nature, can be diluted in any nonaqueous solvent to form the solution of the present invention. More particularly, solvents such as propylene glycol, alcohol, ether, chloroform, ethanol, benzene, carbon disulfide, propyl; alcohol, isopropanol, 2-propanol, fixed and volatile oils, and the like. Combinations of these solvents can also be used.

It is preferable to use a combination of propylene glycol and absolute ethanol as a solvent. It more preferable to use between 90% to 98% propylene glycol and 2% to 10% absolute ethanol, most preferably 94% propylene glycol and 6% absolute ethanol or 5% to 40% isopropanol and 60% to 95% propylene glycol.

In a preferred embodiment, the fatty acids can be microencapsulated and put into a suspension in water.

In yet another preferred embodiment, the fatty acids can be in the form of a shampoo. The major ingredients of the shampoo being known to those skilled in the art.

Fatty acids are commercially available from various chemical companies in solid form. However, since it is difficult to solubilize fatty acids, the fatty acid is generally added to the solvent under constant agitation and at a temperature of between about 37° C. to about 38° C. more preferably about 37.5° C.

Once obtained, the compositions of the present invention can be tested for their efficacy to prevent stress in mammals. Well documented stressors are, for example, the wearing of mammals, the transportation of mammals, and the like. Application of the present composition in the form of a spray, aerosol and the like in an area surrounding the stressful events results in diminution of stress as indicated by a variety of factors such as weight gain, social behavior with respect to other mammals, wounds on the body, especially the ears, salivary cortisol, heart rate, and the like.

Thus, the present composition can be applied to a variety of objects that the mammal comes in contact with such as walls, in the air and toys. Moreover, the present composition can be applied on the skin of mammals.

The above-described compositions were discovered after detailed analysis of the chemical composition of secretions surrounding the mammary glands of sows that were either pregnant or suckling.

More particularly, this procedure involved swabbing the area around the breasts of a sow with a sterile compress and analyzing the chemical composition of the secretions via mass spectroscopy or gas chromatography/mass spectroscopy.

The initial mass spectroscopy experiment together with a statistical analysis revealed that there were four separately identified fractions having varying number of components that make up each fraction. These fractions were then further analyzed by classical statistical analysis to determine the compositions of each fraction.

For example, Fraction 1, named φApc1, was composed of mainly cholesterol and different cyclopentane and cyclohexane proprionic acids. Fraction φApc2 comprised molecules that specifically resembled the state of gestation or pregnancy such as egostanol, γ sitosterol and dermosterol. Fraction 3, called φApc3 was composed mainly of fatty acids, as well as alcohol, glycerol and diesters of glycerol and is specific for suckling sows. Fraction 4, named φApc4 contained methyl esters of palmitic acid and vaccenic acid. This last fraction contains compositions present in both suckling and pregnant sows.

Once the components of each of the fractions was identified, a preferred fraction, φApc3 was used to test its effects on stress and aggressiveness in piglets.

The pheromonal composition of the present invention is not limited to treatment of piglets. The same basic composition or one of similar origin can be obtained and used, for example, in dogs or cats to calm their anxiety after, for example, removal from their familiar surroundings such as being taken to the veterinarian.

Also, the basic composition of the present invention or a similar composition can be used to depress an infant's anxiety when the infant is, for example, separated from its mother or placed in unfamiliar surroundings.

In order to fully illustrate the present invention and advantages thereof, the following specific examples are given, it being understood that the same are intended only as illustrative and in nowise limitative.

EXAMPLE 1

Isolation and analysis of compositions from areas surrounding the mammary glands of sows Mixed breeds of Chinese and European strains of adult female swine or sows that were either suckling or pregnant were used in this example.

The sows were rubbed around the area surrounding their intermammary groove using the sterilized compresses several times. The compress was then placed in a solvent of methanol or acetonitrile.

Fourteen total samples were obtained. Seven samples were obtained from sows that were pregnant and seven other samples were obtained from sows that were suckling.

The fourteen samples were combined and analyzed via mass spectroscopy to determine the composition of the mammary gland secretions.

Mass Spectroscopy

Mass spectroscopy was initially performed using a DB 1 35 m–25 u column. A spectrograph was obtained from the combined samples.

After statistical analysis of the spectrograph, it was determined that the mammary secretions could be divided into four major fractions. These four fractions were composed of a combination of different compounds. These fractions were named φApc1, φApc2, φApc3 and φApc4 and were composed of 38 different components in all.

The following Tables I to IV illustrate the initial findings of this analysis based on the results of the mass spectroscopy.

TABLE I

| | φApc1 | |
|---|---|---|
| Component | Peak (mn) | Identification |
| E1 | 16.96 | N/I |
| E2 | 18.40 | N/I |
| E3 | 26.06 | N/I |
| E4 | 30.99 | dermosterol | wherein N/I means not identified

TABLE II

φApc2

| Component | Peak (mn) | Identification |
|---|---|---|
| E5 | 19.73 | N/I |
| E6 | 21.01 | N/I |
| E7 | 21.15 | C18 acid |
| E8 | 22.22 | N/I |
| E9 | 22.85 | N/I |
| E10 | 22.91 | similar compound to E11 |
| E11 | 23.01 | N/I |
| E12 | 23.16 | similar compound to E9 |
| E13 | 24.57 | N/I |
| E14 | 24.81 | N/I |
| E15 | 26.22 | N/I |
| E16 | 30.40 | cholestan 3ol (3α) |
| E17 | 31.59 | ergost 5 en 3 olβ |
| E18 | 32.06 | ergostanol + $CH_2$ |
| E19 | 32.12 | N/I |
| E20 | 32.45 | γ sitosterol |
| E21 | 32.72 | N/I |
| E22 | 32.82 | N/I |
| E23 | 32.90 | α-amyrin |
| E24 | 33.30 | stigmasta 3,5 di en 7 one |
| E25 | 33.81 | N/I |
| E26 | 34.47 | N/I |

Wherein N/I means not identified

TABLE III

φApc3

| Component | Peak (mn) | Identification |
|---|---|---|
| E27 | 20.38 | C17 Me ester olefine |
| E28 | 20.48 | N/I |
| E29 | 20.60 | C17 Me ester |
| E30 | 21.07 | C16 acid |
| E31 | 21.09 | N/I |
| E32 | 22.64 | N/I |
| E33 | 22.80 | C19 Me ester |
| E34 | 24.19 | N/I |
| E35 | 28.55 | N/I |

Wherein N/I means not identified

TABLE IV

φApc4

| Component | Peak (mn) | Identification |
|---|---|---|
| E36 | 22.30 | C19 Me ester of diene |
| E37 | 22.40 | C19 Me ester of olefine |
| E38 | 30.75 | cholesterol |

Further analysis of the various components in each of the four identified fractions via mass spectroscopy revealed a more thorough identification of the components. These results are set forth in Table V below.

TABLE V

| Component | Peaks | Identification |
|---|---|---|
| E1 | 5.63 | — |
| E2 | 6.59 | — |
| E3 | 11.70 | cyclopentane proprionic acid |
| E4 | 13.15 | cyclohexane proprionic acid |
| E5 | 13.90 | decanoic acid |
| E6 | 15.31 | alcohol |
| E7 | 15.45 | methyl ester/C9 |
| E8 | 16.54 | dodecanoic acid |

TABLE V-continued

| Component | Peaks | Identification |
|---|---|---|
| E9 | 16.75 | methyl ester/C10 |
| E10 | 16.81 | isomer of methyl ester/C10 |
| E11 | 18.87 | tetradecanoic acid |
| E12 | 20.33 | 9-hexadecanoic-methyl ester |
| E13 | 20.55 | methyl ester of palmitic acid |
| E14 | 20.81 | 9-hexadecanoic acid |
| E15 | 21.17 | palmitic acid |
| E16 | 22.22 | methyl ester of 9-12-octadecadenoic acid |
| E17 | 22.37 | methyl ester of 11-octadecanoic acid |
| E18 | 22.58 | methyl ester acid/C18 |
| E19 | 23.15 | linolic acid |
| E20 | 23.26 | oleic acid |
| E21 | 25.98 | propane-triol=glycerol |
| E22 | 27.46 | diester of glycerol by hexadecanoic acid and hexadecanoic acid |
| E23 | 28.47 | alcohol |
| E24 | 30.30 | dihydrocholesterol |
| E25 | 30.68 | cholesterol |
| E26 | 30.90 | dermosterol |
| E27 | 31.25 | dihydrocholesterol + $CH_2$ |
| E28 | 31.93 | ergostanol + $CH_2$ |
| E29 | 32.24 | γ sitosterol |
| E30 | 32.37 | ergostanol + $CH_2$ |

Gas Chromatography/Mass Spectroscopy

The results set forth in Table V were also confirmed using gas chromatography/mass spectroscopy (GC/MS).

A Fissons GC 8000 gas chromatographer and a VG Quattro mass spectrometer was utilized in the analysis. The detection was effectuated on impact using (EI+) at an energy of 70 eV at 180° C. A JW column type DB1 at a split of 1/20 split/splitless 5 seconds was used.

Four swab samples were taken; 2 from pregnant sows and 2 from suckling sows. These samples were diluted in either methanol or acetonitrile. 10 ml of methanol or acetonnitrile was added to a flask containing the swabs and evaporated under nitrogen. 1.0 ml of methanol or acetonitrile was then added to the samples and 1 μl, was injected into the GC/MS.

The following chromatographic profile was obtained on the sample for the suckling sow as set forth in Table VI.

TABLE VI

| Composition | Time of retention (minutes) |
|---|---|
| cyclopentyl-3-propanoic acid | 11.72 |
| cyclohexyl-3-propanoic acid | 13.16 |
| decanoic acid | 13.90 |
| dodecanoic acid | 16.54 |
| methyl 5-decenoate | 16.75 |
| methyl-x-decenoate(isomer) | 16.81 |
| tetradecanoic acid | 18.59 |
| methyl 9-hexadecenoate | 20.33 |
| methyl hexadecenoate | 20.59 |
| 9-hexadecanoic acid | 20.81 |
| hexadecanoic acid | 21.17 |
| methyl 9-12-octadecanoate | 22.27 |
| methyl-9-octadecanoate | 22.37 |
| methyl octadeconoate | 22.62 |
| 9-12-octadecanoic acid | 23.15 |
| 9-octadeconoic acid | 23.15 |
| octadecanoic acid | 23.26 |
| glycerol-2-hexadecanoate | 25.98 |
| glycerol-2-9-12-octadecanoate | 27.46 |
| glycerol-2-octadecanoate | 27.46 |
| cholesterol | 30.73 |

The above spectrophotometric profile is illustrated in FIG. 1.

The following spectrophotometric profile was obtained on the pregnant sow as illustrated in Table VII.

TABLE VII

| Composition | Time of retention (minutes) |
|---|---|
| cyclopentyl-3-propanoic acid | 11.70 |
| cyclohexyl-3-propanoic acid | 13.15 |
| methyl 4-octonoate | 15.45 |
| methyl 5-decenoate | 16.75 |
| methyl x-decenoate (isomer) | 16.81 |
| methyl hexadecanoate | 20.55 |
| methyl, 9-12-octadecanoate | 22.22 |
| methyl, 9-octadecenoate | 22.31 |
| methyl, 11-octadecenoate | 22.38 |
| methyl, octadecanoate | 22.58 |
| nitrile or polyunsaturated alcohol | 28.47 |
| dihydrocholesterol | 30.30 |
| cholesterol | 30.63 |
| desmosterol | 30.85 |
| ergonstanol | 31.14 |
| ergostanol + ($CH_2$ or methyl) | 31.93 |
| gamma sitosterol | 32.24 |
| ergostanol + ($CH_2$ or methyl) | 32.37 |

The above spectrophotometric profile is illustrated in FIG. 2. The GC/MS data confirmed the data present in the mass spectroscopy experiments.

Summary of the Data obtained on the four fractions.

The data set forth above with the identified components can be summarized in the following Tables VIII–XI. These tables include the percentage of each composition.

TABLE VIII

Fraction φApc1

| Composition | Percentage |
|---|---|
| cyclopentanepropanoic acid | 2.9% to 3.9% |
| cyclohexanepropanoic acid | 3.4% to 5.9% |
| methyl ester/C10 | 2.8% to 3.9% |
| cholesterol | 86.3% to 90.9% |

Fraction φApc1 was considered as a "neutral" fraction resembling the compositions present in both batches of pigs.

TABLE IX

Fraction φApc2

| Composition | Percentage |
|---|---|
| E1 | 1.6% to 2.2% |
| E2 | 1.3% to 1.9% |
| methyl ester/C9 | 2.2% to 2.8% |
| isomer of the methyl ester C10 | 2.4% to 3% |
| methyl ester of 9–12 octadecadenoic acid | 16.3% to 16.9% |
| methyl ester of a C18 acid | 4.2% to 4.6% |
| alcohol | 10.7% to 11.3% |
| dihydrocholesterol | 13.8% to 14.4% |
| dermosterol | 11.8% to 12.4% |
| dihydrochoelsterol + $CH_2$ | 4.5% to 5.1% |
| ergostanol + $CH_2$ | 17.5% to 18.1% |
| γ sitosterol | 5.9% to 6.5% |
| ergostanol + $CH_n$ | 3.9% to 4.5% |

Fraction φApc2 comprises molecules that specifically resemble the state of gestation.

TABLE X

Fraction φApc3

| Composition | Percentage |
|---|---|
| capric acid | 0.8% to 1.2% |
| alcohol | 0% to 1.1% |
| lauric acid | 1.7% to 3.6% |
| myristic acid | 2.2% to 3.9% |
| palmitric-methyl ester | 0.3% to 1.8% |
| palmitoleic acid | 2.5% to 6.1% |
| palmitic acid | 10.1% to 13.2% |
| linoleic acid | 19.8% to 22.5% |
| oleic acid | 8.3% to 15.2% |
| glycerol | 14.1% to 18.9% |
| diester of glycerol | 18.5% to 23.2% |

Fraction φApc3 is specific for suckling sows. It comprises 11 different compositions including alcohol, glycerol and diesters of glycerol.

TABLE XI

Fraction φApc4

| Composition | Percentage |
|---|---|
| methyl ester of palmitic acid | 25.5% to 33.5% |
| methyl ester of vaccenic acid | 66.5% to 74.5% |

Fraction φApc4 is a fraction having compositions that are present in two batches of the pigs, but the concentration is considerably higher in suckling sows.

EXAMPLE 2

Formulation of the pheromone

2% by weight capric acid, 5.3% by weight lauric acid, 6.2% by weight myristic acid, 11.2% by weight palmitoleic acid, 20.5% by weight palmitic acid 35.2% by weight linoleic acid and 19.6% by weight oleic acid were mixed with a solvent composed of 94% propylene glycol and 6% absolute alcohol. The mixture was heated to 37.5° C. and constantly mixed until dissolution of the complete crystals.
Preparation of Batch solution Four flasks of 500 ml containing 400 g of the above-solution were prepared for each batch. Also, 8 flasks containing 400 g of propylene glycol, used as a placebo and 4 flasks containing the above formulation at a 5% concentration was also prepared.

The flasks were identified by a color code, which was given due to the size of the pigs. The red flasks were for tiny piglets, and the flasks labeled in black were for large piglets, while the flasks labeled in green were for medium size piglets. The protocol in which each pigpen was treated with the pheromones of the present invention or the placebo was unknown; i.e., a simple blind study.

Visual examination of the flasks revealed no substantial differences between the placebo flasks and the flasks comprising the solution.

EXAMPLE 3

Measurement of bites on the piglets ears

Three batches of 23 piglets per batch having an age of about 26 days were utilized. The red lot had piglets from 5 litters, while the black lot had 4 litters. The piglets were also marked in the appropriate color according to their weight and numbered from 1 to 23.

The different solutions were applied on the walls of the pig pen each day starting at the same time each day, beginning with the red lot, then the black lot and finishing with the green lot.

The number of bites on the ears at 0 hours, 5 hours and 72 hours was measured after application of the pheromones or the placebo. The results are in the following tables.

TABLE XII

0 HOURS: "LIGHT" GROUP (RED)

| No. | EXISTING BITES | NEW BITES | OBSERVATIONS |
|---|---|---|---|
| 1 | 0 | 0 | |
| 2 | 0 | 6 | |
| 3 | 2 | 4 | |
| 4 | 5 | 1 | |
| 5 | 1 | 0 | |
| 6 | 14 | 0 | |
| 7 | 2 | 5 | |
| 8 | 2 | 8 | |
| 9 | 23 | 4 | |
| 10 | 8 | 1 | |
| 11 | 30 | 0 | |
| 12 | 5 | 0 | |
| 13 | 5 | 1 | |
| 14 | 24 | 0 | |
| 15 | 4 | 2 | |
| 16 | 20 | 5 | |
| 17 | 11 | 5 | |
| 18 | 26 | 12 | |
| 19 | 20 | 7 | |
| 20 | 4 | 7 | |
| 21 | 7 | 3 | |
| 22 | 5 | 9 | |
| 23 | 15 | 1 | |

TABLE XIII

0 HOURS: "HEAVY" GROUP (BLACK)

| No. | EXISTING BITES | NEW BITES | OBSERVATIONS |
|---|---|---|---|
| 1 | 1 | 7 | |
| 2 | 4 | 27 | |
| 3 | 6 | 5 | |
| 4 | 8 | 0 | |
| 5 | 3 | 7 | |
| 6 | 20 | 0 | |
| 7 | 8 | 2 | nursing on the others |
| 8 | 8 | 0 | |
| 9 | 1 | 3 | |
| 10 | 7 | 8 | |
| 11 | 15 | 1 | |
| 12 | 3 | 12 | nursing on the others |
| 13 | 5 | 0 | |
| 14 | 12 | 2 | |
| 15 | 4 | 3 | |
| 16 | 7 | 0 | |
| 17 | 6 | 18 | |
| 18 | 8 | 4 | |
| 19 | 2 | 0 | |
| 20 | 5 | 28 | |
| 21 | 4 | 0 | |
| 22 | 8 | 0 | |
| 23 | 3 | 5 | |

TABLE XIV

0 HOURS: "MEDIUM" GROUP (GREEN)

| No. | EXISTING BITES | NEW BITES | OBSERVATIONS |
|---|---|---|---|
| 1 | 29 | 10 | |
| 2 | 47 | 10 | |
| 3 | 48 | 0 | |
| 4 | 19 | 8 | |
| 5 | 55 | 21 | |
| 6 | 19 | 20 | |
| 7 | 16 | 10 | |
| 8 | 31 | 0 | |
| 9 | 16 | 11 | |
| 10 | 16 | 10 | |
| 11 | 10 | 45 | numerous marks on the back |
| 12 | 43 | 3 | |
| 13 | 41 | 27 | |
| 14 | 43 | 5 | |
| 15 | 48 | 28 | |
| 16 | 30 | 20 | |
| 17 | 29 | 20 | |
| 18 | 17 | 21 | |
| 19 | 4 | 4 | |
| 20 | 6 | 0 | |
| 21 | 16 | 20 | |
| 22 | 11 | 30 | |
| 23 | 12 | 16 | |

TABLE XV

5 HOURS: "LIGHT" GROUP (RED)

| No. | EXISTING BITES | NEW BITES | OBSERVATIONS |
|---|---|---|---|
| 1 | 0 | 4 | |
| 2 | 3 | 32 | |
| 3 | 6 | 11 | |
| 4 | 6 | 41 | |
| 5 | 1 | 22 | |
| 6 | 14 | 24 | |
| 7 | 7 | 8 | |
| 8 | 10 | 6 | |
| 9 | 27 | 53 | |
| 10 | 9 | 12 | |
| 11 | 30 | 31 | |
| 12 | 5 | 13 | |
| 13 | 6 | 18 | |
| 14 | 24 | 22 | |
| 15 | 6 | 38 | |
| 16 | 25 | 8 | |
| 17 | 16 | 11 | |
| 18 | 38 | 15 | |
| 19 | 27 | 21 | |
| 20 | 11 | 10 | |
| 21 | 10 | 8 | |
| 22 | 14 | 15 | |
| 23 | 16 | 3 | |

TABLE XVI

5 HOURS: "HEAVY" GROUP (BLACK)

| No. | EXISTING BITES | NEW BITES | OBSERVATIONS |
|---|---|---|---|
| 1 | 8 | 5 | |
| 2 | 31 | 65 | |
| 3 | 11 | 60 | |
| 4 | 8 | 54 | |
| 5 | 10 | 84 | |
| 6 | 20 | 14 | |
| 7 | 10 | 29 | |
| 8 | 8 | 35 | |
| 9 | 4 | 9 | |
| 10 | 15 | 53 | |
| 11 | 16 | 29 | |
| 12 | 15 | 69 | |
| 13 | 5 | 59 | |
| 14 | 14 | 64 | |
| 15 | 7 | 94 | |
| 16 | 7 | 17 | |

TABLE XVI-continued

5 HOURS: "HEAVY" GROUP (BLACK)

| No. | EXISTING BITES | NEW BITES | OBSERVATIONS |
|---|---|---|---|
| 17 | 24 | 9 | |
| 18 | 14 | 18 | |
| 19 | 2 | 92 | |
| 20 | 33 | 57 | |
| 21 | 4 | 11 | |
| 22 | 8 | 55 | |
| 23 | 8 | 13 | |

TABLE XVII

5 HOURS: "MEDIUM" GROUP (GREEN)

| No. | EXISTING BITES | NEW BITES | OBSERVATIONS |
|---|---|---|---|
| 1 | 39 | 5 | |
| 2 | 57 | 6 | |
| 3 | 48 | 10 | |
| 4 | 45 | 0 | |
| 5 | 76 | 1 | |
| 6 | 39 | 1 | |
| 7 | 26 | 1 | |
| 8 | 31 | 5 | |
| 9 | 27 | 5 | |
| 10 | 26 | 19 | |
| 11 | 55 | 9 | |
| 12 | 45 | 0 | |
| 13 | 67 | 6 | |
| 14 | 48 | 1 | |
| 15 | 76 | 22 | |
| 16 | 47 | 0 | |
| 17 | 47 | 0 | |
| 18 | 38 | 5 | |
| 19 | 8 | 3 | |
| 20 | 6 | 2 | |
| 21 | 34 | 0 | |
| 22 | 40 | 0 | |
| 23 | 28 | 14 | |

TABLE XVIII

72 HOURS: "LIGHT" GROUP (RED)

| No. | EXISTING BITES | NEW BITES | OBSERVATIONS |
|---|---|---|---|
| 1 | 13 | 3 | |
| 2 | 11 | 5 | |
| 3 | 7 | 5 | |
| 4 | 41 | 2 | |
| 5 | 44 | 15 | |
| 6 | 32 | 3 | |
| 7 | 86 | 16 | |
| 8 | 6 | 5 | |
| 9 | 72 | 3 | |
| 10 | 16 | 4 | |
| 11 | 67 | 5 | |
| 12 | 3 | 2 | |
| 13 | 28 | 6 | |
| 14 | 56 | 1 | |
| 15 | 81 | 0 | |
| 16 | 48 | 8 | |
| 17 | 86 | 3 | |
| 18 | 54 | 12 | |
| 19 | 54 | 3 | |
| 20 | 9 | 6 | |
| 21 | 16 | 4 | |
| 22 | 47 | 1 | |
| 23 | 32 | 8 | |

TABLE XIX

72 HOURS: "HEAVY" GROUP (BLACK)

| No. | EXISTING BITES | NEW BITES | OBSERVATIONS |
|---|---|---|---|
| 1 | 24 | 22 | body covered with wounds |
| 2 | 40 | 3 | |
| 3 | 68 | 8 | |
| 4 | 49 | 7 | |
| 5 | 99 | 1 | |
| 6 | 34 | 4 | |
| 7 | 33 | 5 | wounds on head |
| 8 | 36 | 4 | |
| 9 | 31 | 12 | |
| 10 | 58 | 14 | body covered with wounds |
| 11 | 45 | 3 | |
| 12 | 46 | 18 | body covered with wounds |
| 13 | 49 | 9 | |
| 14 | 60 | 4 | |
| 15 | 71 | 2 | |
| 16 | 23 | 0 | |
| 17 | 10 | 13 | |
| 18 | 38 | 4 | |
| 19 | 80 | 1 | |
| 20 | 65 | 4 | |
| 21 | 34 | 8 | |
| 22 | 38 | 3 | |
| 23 | 26 | 4 | |

TABLE XX

72 HOURS: "MEDIUM" GROUP (GREEN)

| No. | EXISTING BITES | NEW BITES | OBSERVATIONS |
|---|---|---|---|
| 1 | 33 | 0 | body covered with wound |
| 2 | 54 | 1 | |
| 3 | 58 | 2 | |
| 4 | 35 | 0 | |
| 5 | 57 | 0 | |
| 6 | 33 | 0 | |
| 7 | 45 | 0 | |
| 8 | 44 | 0 | |
| 9 | 62 | 1 | |
| 10 | 30 | 4 | |
| 11 | 62 | 0 | |
| 12 | 38 | 0 | |
| 13 | 126 | 0 | |
| 14 | 69 | 0 | |
| 15 | 54 | 24 | |
| 16 | 31 | 1 | |
| 17 | 38 | 0 | |
| 18 | 70 | 1 | |
| 19 | 5 | 4 | |
| 20 | 46 | 1 | |
| 21 | 11 | 0 | |
| 22 | 32 | 0 | |
| 23 | 72 | 2 | |

Example 4

Video Camera Review of Piglets Behavior During Testing

Two video cameras were placed to observe the piglets during testing and the piglets were observed for 45 minutes. After filming the first experiment, four parameters were utilized to note the piglets behavior.

The films were read twice in this evaluation and a detailed sequence of events was provided. The value obtained was the mean value. One reading was retained for the duration.

The following items were reviewed on the films:

(1) Number of aggressions with bites

This item was evaluated as follows in the film. The piglet aggressor inflicts on his adversary one or more bites on the body (ears, shoulders, etc.) and pulls away.

By convention, the behavior of the attacking piglet was deduced, as well as the retaliation of the adversary piglet.

When the battle was prolonged by a chain of many retaliations and contra-retaliations, it was judged as a single aggression. This measure was taken for a total of 45 minutes of filming.

(2) Duration of combat

The duration of combat was measured from the onset of the first bite inflicted until the first 3 second pause from fighting. The time of combat was expressed in seconds.

(3) Number of playing sessions

This observation was based on a number of activities which were not part of the other identified categories such as aggression, eating, exploration, etc. The sequences were implicated in 1 to n piglets. Two subitems were identified such as solitary playing and group playing.

(4) Number of aggressions with biting/Number of touching incidents

The number of aggressions by biting was defined under section 1 and the measurement taken was the same for this section. The touching contacts were those in which direct physical contact between two piglets was noted. Also noted was the nature of the contact; i.e., either passive or aggressive.

The results of the observations are set forth below:

Assault's Number with Bite—"Light" Group (Red)

| FIRST READING | SECOND READING | AVERAGE |
| --- | --- | --- |
| 87 | 93 | 90 |

Assault's Number with Bite—"Medium" Group (Green)

| FIRST READING | SECOND READING | AVERAGE |
| --- | --- | --- |
| 18 | 19 | 18.5 |

Number of Playing Sequences—"Light" Group (Red)

| FIRST READING | SECOND READING | AVERAGE |
| --- | --- | --- |
| 1 | 4 | 2.5 |

Number of Playing Sequences—"Medium" Group (Green)

| FIRST READING | SECOND READING | AVERAGE |
| --- | --- | --- |
| 53 | 62 | 57.5 |

TABLE XXI

LENGTH OF FIGHTS - "LIGHT" GROUP (RED)

| Fight No. | Length of fight in seconds |
| --- | --- |
| 1 | 11 |
| 2 | 9 |
| 3 | 6 |
| 4 | 12 |
| 5 | 24 |
| 6 | 9 |
| 7 | 5 |
| 8 | 31 |
| 9 | 20 |
| 10 | 14 |
| 11 | 8 |
| 12 | 5 |
| 13 | 23 |
| 14 | 14 |
| 15 | 17 |
| 16 | 12 |
| 17 | 10 |
| 18 | 9 |
| 19 | 6 |
| 20 | 13 |
| 21 | 26 |
| 22 | 20 |
| 23 | 37 |
| 24 | 14 |
| 25 | 6 |
| 26 | 15 |
| 27 | 13 |
| 28 | 24 |
| 29 | 20 |
| 30 | 10 |
| 31 | 26 |
| 32 | 9 |
| 33 | 18 |
| 34 | 21 |
| 35 | 9 |
| 36 | 7 |
| 37 | 33 |
| 38 | 20 |
| 39 | 6 |
| 40 | 4 |
| 41 | 11 |
| 42 | 9 |
| 43 | 6 |
| 44 | 8 |
| 45 | 10 |
| 46 | 12 |
| 47 | 9 |
| 48 | 3 |
| 49 | 8 |
| 50 | 6 |
| 51 | 5 |
| 52 | 12 |
| 53 | 21 |
| 54 | 17 |
| 55 | 6 |
| 56 | 4 |
| 57 | 18 |
| 58 | 15 |
| 59 | 25 |
| 60 | 9 |
| 61 | 12 |
| 62 | 4 |
| 63 | 6 |

TABLE XXI-continued

LENGTH OF FIGHTS - "LIGHT" GROUP (RED)

| Fight No. | Length of fight in seconds |
|---|---|
| 64 | 10 |
| 65 | 9 |
| 66 | 6 |
| 67 | 5 |
| 68 | 3 |
| 69 | 11 |
| 70 | 24 |
| 71 | 15 |
| 72 | 9 |
| 73 | 15 |
| 74 | 23 |
| 75 | 14 |
| 76 | 10 |
| 77 | 19 |
| 78 | 6 |
| 79 | 8 |
| 80 | 17 |
| 81 | 11 |
| 82 | 7 |
| 83 | 13 |
| 84 | 9 |
| 85 | 11 |
| 86 | 12 |
| 87 | 14 |

TABLE XXII

LENGTH OF FIGHTS - "MEDIUM" GROUP (GREEN)

| Fight No. | Length of fight in seconds |
|---|---|
| 1 | 3 |
| 2 | 8 |
| 3 | 5 |
| 4 | 2 |
| 5 | 6 |
| 6 | 7 |
| 7 | 5 |
| 8 | 9 |
| 9 | 3 |
| 10 | 3 |
| 11 | 5 |
| 12 | 5 |
| 13 | 8 |
| 14 | 3 |
| 15 | 9 |
| 16 | 4 |
| 17 | 7 |
| 18 | 5 |

Number of Assaults/Number of Contacts: "Light" Group (Red)

| NUMBER OF ASSAULTS 1ST READING | NUMBER OF CONTACTS 1ST READING | NUMBER OF ASSAULTS 2ND READING | NUMBER OF CONTACTS 2ND READING |
|---|---|---|---|
| 87 | 103 | 93 | 105 |
| RATIO = 84.5% | | RATIO = 88.6% | |
| | RATIO = 86.5% | | |

Number of Assaults/Number of Contacts: "Medium" Group (Green)

| NUMBER OF ASSAULTS 1ST READING | NUMBER OF CONTACTS 1ST READING | NUMBER OF ASSAULTS 2ND READING | NUMBER OF CONTACTS 2ND READING |
|---|---|---|---|
| 18 | 124 | 19 | 123 |
| RATIO = 14.5% | | RATIO = 15.4% | |
| | RATIO = 14.9% | | |

Weight Results

Each piglet was weighed at 0 hours and at 72 hours. The following results were obtained:

Weight—"Light" Group (Red)

| Weight 0 Hours | Weight 72 Hours | Weight gain at 72 Hours from 0 Hours | Weight gain from 0 Hours in percentage |
|---|---|---|---|
| 120 Kg | 134 Kg | 14 Kg | 11.66% |

Weight—"Heavy" Group (Black)

| Weight 0 Hours | Weight 72 Hours | Weight gain at 72 Hours from 0 Hours | Weight gain from 0 Hours In percentage |
|---|---|---|---|
| 189 Kg | 207 Kg | 18 Kg | 9.52% |

Weight—"Medium" Group (Green)

| Weight 0 Hours | Weight 72 Hours | Weight gain at 72 Hours from 0 Hours | Weight gain from 0 Hours in percentage |
|---|---|---|---|
| 153 Kg | 169 Kg | 16 Kg | 10.45% |

Analysis of Results

The results were analyzed using a Statview F-4.5 computer software.

A comparison was made of the scores obtained by each batch of the piglet at 0 hours. This analysis resulted in a result of fresh and old bites that were significant in the medium sized piglets. This result excluded the possibility of using the total number of bites in the course of the analysis.

| | Mean deviation | Degrees of freedom (DDL) | t | p |
|---|---|---|---|---|
| red, green | −17.522 | 44 | −4.524 | <.0001 |
| red, black | 3.696 | 44 | 1.712 | .0940 |
| green, black | 21.217 | 44 | 6.107 | <.0001 |

| | Number | Average | Variance | Std dev | Std error |
|---|---|---|---|---|---|
| red | 23 | 10.130 | 87.300 | 9.343 | 1.948 |
| green | 23 | 27.652 | 257.692 | 16.053 | 3.347 |
| black | 23 | 6.435 | 19.893 | 4.460 | .930 |

-continued

|  | Mean deviation | Degrees of freedom -(DDL) | t | p |
|---|---|---|---|---|
| red, green | −11.217 | 44 | −4.549 | <.0001 |
| red, black | −2.217 | 44 | −1.196 | .2382 |
| green, black | 9.000 | 44 | 3.090 | .0035 |

|  | Number | Average | Variance | Std der | Std error |
|---|---|---|---|---|---|
| red | 23 | 3.522 | 11.897 | 3.449 | .719 |
| green | 23 | 14.739 | 127.929 | 11.311 | 2.358 |
| black | 23 | 5.739 | 67.202 | 8.198 | 1.709 |

Further analysis was performed by comparing the mean of the new bites for each batch of piglets at 5 hours and 72 hours with the help of the student T test.

T-Test Series Non-Matched for 5 Hours—Fresh Bites

Variable Group

|  | Mean deviation | Degrees of freedom (DDL) | t | p |
|---|---|---|---|---|
| red, green | 13.522 | 44 | 4.518 | <.0001 |
| red, black | −24.739 | 44 | −3.807 | .0004 |
| green, black | −38.261 | 44 | −6.327 | <.0001 |

Information Concerning 5 Hours—Fresh Bites

Variable Group

|  | Number | Average | Variance | Std dev | Std error |
|---|---|---|---|---|---|
| red | 23 | 18.522 | 167.988 | 12.961 | 2.703 |
| green | 23 | 5.000 | 38.000 | 6.164 | 1.285 |
| black | 23 | 43.261 | 803.020 | 28.338 | 5.909 |

T-Test Series Non-Matched for 72 Hours—Fresh Bites

Variable Group

|  | Mean deviation | Degrees of Freedom DDL | t | p |
|---|---|---|---|---|
| red, green | 3.435 | 44 | 2.528 | .0151 |
| red, black | −1.435 | 44 | −.974 | .3352 |
| green, black | −4.870 | 44 | −3.087 | .0035 |

Information Concerning 72 Hours—Fresh Bites

Variable Group

|  | Number | Average | Variance | Std dev | Std error |
|---|---|---|---|---|---|
| red | 23 | 5.217 | 17.542 | 4.188 | .873 |
| green | 23 | 1.783 | 24.905 | 4.991 | 1.041 |
| black | 23 | 6.652 | 32.328 | 5.686 | 1.186 |

T-Test Series Non-Matched For 5 Hours—Fresh Bites
Variable Group: Treated

|  | Mean deviation | Degrees of Freedom DDL | t | p |
|---|---|---|---|---|
| placebo, pheromone | 25.891 | 67 | 4.853 | >.0001 |

Information Concerning 5 Hours Fresh Bites
Variable Group: Treated

|  | Number | Average | Variance | Std dev | Std error |
|---|---|---|---|---|---|
| placebo | 46 | 30.891 | 631.121 | 25.122 | 3.704 |
| pheromone | 23 | 5.000 | 38.000 | 6.164 | 1.285 |

Information Concerning 72 Hours—Fresh Bites
Variable Group

|  | Mean deviation | Degrees of freedom (DDL) | t | p |
|---|---|---|---|---|
| placebo, pheromone | 4.152 | 67 | 3.258 | .0018 |

T-Test Series Non-Matched For 72 Hours—Fresh Bites
Variable Group: Treated

|  | Number | Average | Variance | Std dev | Std error |
|---|---|---|---|---|---|
| placebo | 46 | 5.935 | 24.907 | 4.991 | .736 |
| pheromone | 23 | 1.783 | 24.905 | 4.991 | 1.041 |

FIGS. 3 and 4 illustrate the above-results in graphic form. In each case, it can be seen that the group of piglets receiving the placebo had more bites that the piglets receiving the pheromone of the present invention.

A further statistical analysis was performed utilizing the number of wound on the ears of the piglets at 0 hours and 72 hours.

T-Test Series Non-Matched For Wounds Between 0 Hours and 72 Hours
Variable Group: Treated

|  | Mean deviation | Degrees of freedom (DDL) | t | p |
|---|---|---|---|---|
| placebo, pheromone | 28.696 | 67 | 4.807 | <.0001 |

Information Concerning the Wounds Between 0 Hours and 72 Hours
Variable Group: Treated

|  | Number | Average | Variance | Std dev | Std error |
|---|---|---|---|---|---|
| placebo | 46 | 35.957 | 557.820 | 23.618 | 3.482 |
| pheromone | 23 | 7.261 | 522.747 | 22.864 | 4.767 |

It can be seen from these results that the piglets receiving the pheromone treatment of the present invention had less wound that the piglets receiving the placebo.

Analysis of Video Observations

The video observations were next compared and analyzed.

Comparison of the Two Groups for the Duration of Fighting

T-Test Non-Matched for the Duration of Fighting
Variable Group: Treated

|  | Mean deviation | Degrees of freedom (DLL) | t | p |
|---|---|---|---|---|
| placebo, pheromone | 7.439 | 103 | 4.331 | <.0001 |

Information of the Group for the Duration of Fighting
Variable Group: Treated

|  | Number | Average | Variance | Std dev | Std error |
|---|---|---|---|---|---|
| placebo | 87 | 12.828 | 51.749 | 7.194 | .771 |
| pheromone | 18 | 5.389 | 4.840 | 2.200 | .519 |

FIG. 5 is a graph illustrating the results with treatment and with placebo concerning the duration of combat of the piglets. It can be shown from this analysis that the treated piglets were significantly less aggressive having a fewer number of battles and for a shorter duration than those piglets in the placebo group. Furthermore, it was observed that the treated piglets were more sociable and had touching contact and played more than the placebo group.

Weight Measurements

The statistical analysis for weight gain, after seventy two hours is set forth below.

T-Test Non Matched for Weight Gain at 72 Hours
Variable Group: Treated

|  | Mean deviation | Degrees of freedom (DDL) | t | p |
|---|---|---|---|---|
| placebo, pheromone | .140 | 67 | .618 | .5385 |

Information Concerning Weight Gain at 72 Hours
Variable Group: Treated

|  | Number | Average | Variance | Std dev | Std error |
|---|---|---|---|---|---|
| placebo | 46 | 10.590 | 1.170 | 1.082 | .160 |
| pheromone | 23 | 10.450 | .000 | .000 | .000 |

Conclusions

It can be concluded from the above testing and analysis that the piglets treated with the peromones of the present invention were more calm, less aggressive and more sociable than their placebo counterparts. In fact, the piglets receiving the placebo were 86% more aggressive and thus were more stressed than their treated counterparts.

It is clear that fighting is associated with a rise in cortisol level and thereby decreases the food conversion efficiency in the piglets. This resulted in a loss of weight for the non-treated placebo group compared with their treated counterparts.

Example 5

Evaluation of the Effect of Two Porcine Pheromones for Aggressive Behavior Among Weaning Piglets The piglets utilized in these experiments weighed 6 to 9 kg and were of the variety Penarlan crossed with Naima. The experiment utilized 5 to 7 sows. 48 hours after birth, the piglets are toothless and tailless. They received an injection of iron at this moment. The male piglets were castrated at 15 days. The weaning took effect at day 22 and different litters were regrouped at day 26 after weaning. There were three groups that were classified according to weight. A light group, a medium group and a heavy group were the classifications utilized in this experiment.

The experiment began with spraying each pig pen with the pheromone composition of the present invention or a placebo.

The PAP1 composition comprised 2% by weight capric acid, 5.3% by weight lauric acid, 6.2% by weight myristic acid, 20.5% by weight palmitic acid, 35.2% by weight linoleic acid and 30.8% by weight oleic acid in 10% polypropylene glycol.

The placebo only contained polypropylene glycol.

The treatment was applied at the same time every day via spraying on all of the walls of the pig pen approximately 15 cm from the floor for four days.

At 0 hours the piglets were captured, identified by placing a tag on their ear, and examined for wounds. Then, the piglets were weighed and classified according to their weight, and placed into three weight groups: light, medium and heavy. The piglets were then placed into pig pens that were previously sprayed with PAP1 or PAP2 or placebo.

Five hours later, the piglets were captured and their wounds counted. The treatment was reapplied the second, third and fourth days at the same hour. On the last day of the experiment day 4, the wounds were reevaluated in the same way for each group.

In the case of PAP2 and the placebo, the treatment was prolonged for four weeks.

No psychotrophic drugs were administered during the testing to any of the piglets.

Video Film

A video film was installed in two pig pens that was used to evaluate the piglets agonostic behavior. The piglets were observed for 45 minutes after their initial regroupment. The film was analyzed as set forth above, for the duration of fighting, the number of fights and the number of peaceful contacts.

Evaluation of the wounds on the ears

The wounds were evaluated on each piglet using the following criteria:

(1) The number of wounds was noted, whether recent or old on the surface or the external or internal parts of the ears.

(2) All wounds that had no continuity with the other wounds were considered as single wounds.

(3) Only the wounds measuring more than 5 mm were counted.

(4) A crusty wound having contact with a recent wound was counted as two (2) wounds.

Results: the following Table XXIII is a summary of the result

TABLE XXIII

|  | piglet No. | bites 0 hours | bites 5 hours | bites between 5–0 hours | treatment | weight 0 hours in kg | weight 7 hours in kg |
|---|---|---|---|---|---|---|---|
| 1 | T-1 | 64 | 96 | 32 | placebo | 7.5 | 10.5 |
| 2 | T-2 | 40 | 66 | 26 | placebo | 6.5 | 8.5 |
| 3 | T-3 | 30 | 45 | 15 | placebo | 6.5 | 8.0 |
| 4 | T-4 | 21 | 35 | 14 | placebo | 4.0 | 6.5 |
| 5 | T-5 | 52 | 82 | 30 | placebo | 7.0 | 9.5 |
| 6 | T-6 | 25 | 33 | 8 | placebo | 5.5 | 7.5 |
| 7 | T-7 | 11 | 11 | 0 | placebo | 7.0 | 10.0 |

TABLE XXIII-continued

| piglet No. | bites 0 hours | bites 5 hours | bites between 5–0 hours | treatment | weight 0 hours in kg | weight 7 hours in kg |
|---|---|---|---|---|---|---|
| 8 T-8 | 47 | 64 | 17 | placebo | 8.5 | 11.5 |
| 9 T-9 | 29 | 39 | 10 | placebo | 5.0 | 7.0 |
| 10 T-10 | 11 | 17 | 6 | placebo | 7.0 | 9.0 |
| 11 T-11 | 70 | 76 | 5 | placebo | 6.5 | 9.5 |
| 12 T-12 | 47 | 52 | 5 | placebo | 7.5 | 11.0 |
| 13 T-13 | 17 | 25 | 8 | placebo | 4.5 | 6.5 |
| 14 T-14 | 44 | 54 | 10 | placebo | 6.0 | 8.0 |
| 15 T-15 | 40 | 45 | 5 | placebo | 5.6 | 8.5 |
| 16 PAP1-1 | 8 | 23 | 15 | -PAP1 | 6.5 | 7.0 |
| 17 PAP1-2 | 40 | 40 | 0 | -PAP1 | 8.0 | 10.0 |
| 18 PAP1-3 | 55 | 92 | 37 | -PAP1 | 7.5 | 9.0 |
| 19 PAP1-4 | 4 | 12 | 8 | -PAP1 | 6.0 | 7.5 |
| 20 PAP1-5 | 11 | 16 | 5 | -PAP1 | 7.0 | 9.5 |
| 21 PAP1-6 | 9 | 18 | 9 | -PAP1 | 4.5 | 6.0 |
| 22 PAP1-7 | 13 | 13 | 0 | -PAP1 | 6.5 | 9.5 |
| 23 PAP1-8 | 11 | 11 | 0 | -PAP1 | 5.0 | 6.5 |
| 24 PAP1-9 | 9 | 15 | 6 | -PAP1 | 6.5 | 9.0 |
| 25 PAP1-10 | 14 | 14 | 14 | -PAP1 | 6.0 | 8.5 |
| 26 PAP1-11 | 4 | 16 | 12 | -PAP1 | 4.5 | 8.0 |
| 27 PAP1-12 | 10 | 16 | 6 | -PAP1 | 6.0 | 9.0 |
| 28 PAP1-13 | 43 | 55 | 12 | -PAP1 | 8.0 | 11.5 |
| 29 PAP1-14 | 31 | 49 | 8 | -PAP1 | 7.5 | 10.0 |
| 30 PAP1-15 | 56 | 56 | 0 | -PAP1 | 7.5 | 9.0 |
| 31 PAP2-1 | 49 | 49 | 8 | PAP2 | 6.5 | 8.0 |
| 32 PAP2-2 | 45 | 47 | 2 | PAP2 | 7.5 | 10.0 |
| 33 PAP2-3 | 31 | 33 | 2 | PAP2 | 8.0 | 10.0 |
| 34 PAP2-4 | 46 | 46 | 0 | PAP2 | 6.0 | 7.5 |
| 35 PAP2-5 | 13 | 14 | 1 | PAP2 | 4.5 | 7.0 |
| 36 PAP2-6 | 56 | 57 | 1 | PAP2 | 7.5 | 10.0 |
| 37 PAP2-7 | 33 | 34 | 1 | PAP2 | 5.5 | 8.0 |
| 38 PAP2-8 | 40 | 44 | 4 | PAP2 | 6.5 | 10.0 |
| 39 PAP2-9 | 11 | 11 | 0 | PAP2 | 7.0 | 9.5 |
| 40 PAP2-10 | 34 | 34 | 0 | PAP2 | 7.0 | 9.5 |
| 41 PAP2-11 | 39 | 43 | 4 | PAP2 | 6.0 | 9.0 |
| 42 PAP2-12 | 48 | 48 | 0 | PAP2 | 6.5 | 9.0 |
| 43 PAP2-13 | 5 | 5 | 0 | PAP2 | 4.5 | 6.5 |
| 44 PAP2-14 | 11 | 12 | 1 | PAP2 | 6.5 | 7.0 |
| 45 PAP2-15 | 22 | 25 | 3 | PAP2 | 4.5 | 9.5 |

Analysis

The weight groups were compared statistically via a T test or using non-parametric parameters. The variation was studied on a number of wounds at 5 hours in the case of valid-randomization of the difference in the number of wounds and at 0 hours and 5 hours in the case of non-valid randomization.

U of Mann-Whitney for BITES between 5 hours-0 hours Group Variables: treatment Exclusion of lines: PAP-2-DATA

| U | 84.000 |
|---|---|
| U Prim | 141.000 |
| Value of z | −1.182 |
| Value of p | .2372 |
| z corrected for ex-aequo | −1.188 |
| p corrected for ex-aequo | .2346 |
| # ex-aequo | 8 |

Information re. Mann-Whitney for BITES between 5 hours-0 hours Group variables: treatment Exclusion of lines: PAP-2-DATA

| | Number | Sum of ranks | Average of ranks |
|---|---|---|---|
| placebo | 15 | 261.000 | 17.400 |
| -PAP1 | 15 | 204.000 | 13.600 |

U of Mann-Whitney for BITES between 5 hours-0 hours Variable Group: treatment Exclusion of lines: PAP-2 -DATA

| U | 12.000 |
|---|---|
| U Prim | 213.000 |
| Value of z | −4.169 |
| Value of p | <.0001 |
| z corrected for ex-aequo | −4.202 |
| p corrected for ex-aequo | <.0001 |
| # ex-aequo | 8 |

Information re. Mann-Whitney for BITES between 5 hours-0 hours Group variables: treatment Exclusion of lines: PAP-2-DATA

| | Number | Sum of ranks | Average of ranks |
|---|---|---|---|
| PAP2 | 15 | 132.000 | 8.800 |
| placebo | 15 | 333.000 | 22.200 |

Weight Gain

The results of the ear wounding experiments showed a means of 12.8 bites in the placebo group, compared to 7.8 bites in the piglets treated with PAP1 and 1.3 bites in the piglets treated with PAP2. When the distribution was not normal, the results were analyzed with a nonparametric test as described by Mann-Whitney that display the differences very significant between the three treatments and show the efficacy of treatment with PAP2.

After 4 weeks of treatment, the piglets were weighed one time a week and the daily weight gain (DWG) at day 21 were compared. The following statistical analysis was obtained.

U of Mann-Whitney for DWG Group variables: treatment Exclusion of lines: PAP-2-DATA

| U | 42.000 |
|---|---|
| U Prim | 183.000 |
| Value of z | −2.924 |
| Value of p | .0035 |
| z corrected for ex-aequo | −2.947 |
| p corrected for ex-aequo | .0032 |
| # ex-aequo | 8 |

Information concerning Mann-Whitney for DWG Group variables: treatment Exclusion of lines: PAP-2-DATA

| | Number | Ranks sum | Ranks average |
|---|---|---|---|
| PAP2 | 15 | 303.000 | 20.200 |
| placebo | 15 | 162.000 | 10.800 |

ANOVA's table for DWG Exclusion of lines: PAP-2-DATA

|  | Degrees of freedom (DDL) | Square sum | Medium square | Value of F | Value of p |
|---|---|---|---|---|---|
| treatment | 2 | .038 | .019 | 3.228 | .0704 |
| waste | 14 | .083 | .006 |  |  |

Model II estimate of variant components: 0.002. Table of means for DWG Effects: treatment Exclusion of lines: PAP-2-DATA

|  | Number | Means | Std. dev | Std. error |
|---|---|---|---|---|
| PAP2 | 6 | .361 | .070 | .028 |
| placebo | 5 | .243 | .088 | .039 |
| -PAP1 | 6 | .313 | .074 | .030 |

PLSD of Fisher for DWG Effects: treatment Level of signif. 5% Exclusion of lines: PAP-2-DATA

|  | Medium deviation | Critical deviation | Value of p |  |
|---|---|---|---|---|
| PAP2, placebo | .118 | .100 | .0238 | S |
| PAP2, -PAP1 | .048 | .095 | .3023 |  |
| placebo, PAP1 | −.071 | .100 | .1521 |  |

Piglets of an initial weight less or equal to 6 Kg
ANOVA's table for DWG Exclusion of lines: PAP-2-DATA

|  | Degrees of freedom (DDL) | Square sum | Medium square | Value of F | Value of p |
|---|---|---|---|---|---|
| treatment | 2 | .027 | .014 | 2.336 | .1175 |
| residues | 25 | .146 | .006 |  |  |

Model II estimate of variant components: 0.001
Table of moyennes for DWG Effects: treatment Exclusion of lines: PAP-2-DATA

|  | Number | Means | Std. dev | Std. error |
|---|---|---|---|---|
| PAP2 | 9 | .354 | .078 | .026 |
| placebo | 10 | .288 | .078 | .025 |
| -PAP1 | 9 | .352 | .073 | .024 |

PLSD of Fisher for DWG Effects: treatment Level of signif. 5% Exclusion of lines: PAP-2-DATA

|  | Medium deviation | Critical deviation | Value of p |
|---|---|---|---|
| PAP2, placebo | .068 | .072 | .0701 |
| PAP2, -PAP1 | .003 | .074 | .9420 |
| placebo, PAP1 | −.064 | .072 | .0813 |

Piglets of an initial weight over 6 Kg
The overall results are set forth in Table XXIV.

TABLE XXIV

|  | sex | DWG at day 7 | weight at day 14 in kg | DWG at day 14 | weight at day 21 in kg | DWG at day 21 |
|---|---|---|---|---|---|---|
| 1 | male | .429 | 13.5 | .429 | 14.5 | .333 |
| 2 | male | .286 | 9.5 | .214 | 10.5 | .190 |
| 3 | female | .214 | 10.0 | .250 | 11.5 | .238 |
| 4 | male | .357 | 7.5 | .250 | 9.5 | .262 |
| 5 | female | .357 | 11.0 | 286 | 11.5 | .214 |
| 6 | female | .286 | 9.0 | .250 | 11.0 | .262 |
| 7 | male | .429 | 12.5 | .393 | 14.5 | .357 |
| 8 | male | .429 | 14.0 | .393 | 14.5 | .286 |
| 9 | female | .288 | 9.0 | .286 | 10.5 | .262 |
| 10 | male | .286 | 10.0 | .214 | 12.5 | .262 |
| 11 | male | .286 | 10.0 | .250 | 13.0 | .310 |
| 12 | female | .500 | 13.5 | .429 | 17.0 | .452 |
| 13 | female | .286 | 5.5 | .071 | 6.5 | .095 |
| 14 | male | .286 | 10.0 | .286 | 13.0 | .333 |
| 15 | female | .286 | 10.5 | .288 | 11.5 | .238 |
| 16 | female | .071 | 9.5 | .214 | 12.0 | .262 |
| 17 | female | .286 | 14.0 | .429 | 16.0 | .381 |
| 18 | female | .214 | 12.0 | .321 | 14.0 | .310 |
| 19 | female | .214 | 9.5 | .250 | 12.0 | .286 |
| 20 | female | .357 | 12.5 | .393 | 14.5 | .357 |
| 21 | male | .214 | 6.5 | .286 | 10.0 | .262 |
| 22 | female | .429 | 12.5 | .429 | 14.5 | .381 |
| 23 | female | .214 | 8.5 | .250 | 10.0 | .238 |
| 24 | male | .357 | 12.0 | .393 | 13.0 | .310 |
| 25 | female | .357 | 10.0 | .288 | 12.0 | .286 |
| 26 | male | .500 | 10.5 | .429 | 12.5 | .381 |
| 27 | male | .429 | 13.0 | .500 | 15.0 | .429 |
| 28 | male | .500 | 16.0 | .571 | 18.0 | .478 |
| 29 | female | .357 | 14.0 | .484 | 16.5 | .429 |
| 30 | male | .214 | 10.5 | .214 | 13.0 | .262 |
| 31 | female | .214 | 11.5 | .357 | 14.0 | .357 |
| 32 | female | .357 | 13.0 | .393 | 14.5 | .333 |
| 33 | male | .286 | 13.0 | .357 | 15.5 | .357 |
| 34 | female | .214 | 10.0 | .286 | 13.5 | .357 |
| 35 | female | .357 | 8.5 | .286 | 10.5 | .286 |
| 36 | male | .357 | 15.5 | .571 | 17.5 | .476 |
| 37 | male | .357 | 12.0 | .464 | 12.5 | .333 |
| 38 | female | .500 | 13.5 | .520 | 15.5 | .429 |
| 39 | female | .357 | 12.5 | .393 | 14.5 | .357 |
| 40 | male | .357 | 12.5 | .393 | 14.0 | .333 |
| 41 | female | .429 | 22.5 | .464 | 14.5 | .405 |
| 42 | female | .357 | 11.5 | .357 | 14.0 | .357 |
| 43 | male | .286 | 8.5 | .286 |  |  |
| 44 | male | .071 | 8.5 | .143 |  |  |
| 45 | female | .714 | 12.5 | .571 |  |  |

FIGS. 6 to 8 illustrate growth curves of the piglets using the placebo, PAP1 or PAP2. In all cases the growth of the piglets subjected to PAP1 or PAP2 treatment was higher than the placebo at 21 days.

The difference in weight was significant for the piglets that had an initial weight that was inferior to 6 kg. The piglets having the heaviest weights still increased in weight after the 21 day weighing after treatment with either pheromone.

Furthermore, it should be observed that the piglets having an initial weight inferior to 6 kg that received the treatment, gained weight to such an extent that they arrived at the mean weight of the heavy counterparts on day 21.

The other comparisons taken on the video wee not subjected to statistical analysis.

Example 6

Effect on Feeding Behavior of Dogs in an Unknown Place

A population of 10 dogs admitted for minor surgery at a veterinary hospital and unaffected in their general health conditions are selected for their study.

The cages of 5 dogs are sprayed with a polypropylene glycol control. The other cages of 5 dogs is sprayed with the composition PAP-1 of the present invention.

After surgery, the dogs are placed in their respective cages and all of these cages are provided with food and water.

The dogs whose cages are sprayed with the pheromone ate more food and appeared to be more relaxed after surgery that the dogs in the central.

Example 7

Control of Anxiety in Infants

Two groups of kindergarten children attending their first day of school are used in this study. In the first group, the walls of the classroom are sprayed with the control of polypropylene glycol. In the second group, the walls of the classroom are sprayed with PAP-1 of the present invention.

The behavior of the children are observed after initial separation from their parents. It is observed that in the control group, the children were more anxious exhibiting such symptoms such as crying and fighting with each other after their parents left.

In the PAP-1 group, the children appear more relaxed and behaved in a less stressful manner.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

What is claimed is:

1. A process to reduce mortality and morbidity during infection in a mammal, said process comprising administering to a mammal in need of such treatment a solution comprising palmitic acid, oleic acid, linoleic acid and derivatives thereof as main active ingredients.

2. The process according to claim 1, wherein said solution comprises between about 18% to 31.2% (w %/w %) palmitic acid, about 34.3% to 47.2% (w %/w %) linoleic acid, about 28.7% to 42.8% (w %/w %) oleic acid and derivatives thereof.

3. The process according to claim 1, wherein said solution comprises between about 18% to 31.2% (w %/w %) palmitic acid, about 34.3% to 47.2% (w %/w %) linoleic acid, about 8.7% to 16% (w %/w %) palmitoleic acid, about 15.7% to 30.7% (w %/w %) oleic acid and derivatives thereof.

4. The process according to claim 1, wherein said solution is in the form of a spray, an aerosol, a shampoo, is microencapsulated or is a slow release matrix.

5. The process according to claim 1, wherein said solution is administered by applying said solution on walls, on skins of mammals, in the air or on toys.

* * * * *